United States Patent
Shen et al.

(10) Patent No.: US 12,087,007 B2
(45) Date of Patent: Sep. 10, 2024

(54) VISION-BASED 6DOF CAMERA POSE ESTIMATION IN BRONCHOSCOPY

(71) Applicant: Auris Health, Inc., Redwood City, CA (US)

(72) Inventors: Mali Shen, Sunnyvale, CA (US); Menglong Ye, Mountain View, CA (US)

( * ) Notice: Subject to any disclaimer, the term of this patent is extended or adjusted under 35 U.S.C. 154(b) by 240 days.

(21) Appl. No.: 17/219,804

(22) Filed: Mar. 31, 2021

(65) Prior Publication Data
US 2022/0319031 A1    Oct. 6, 2022

(51) Int. Cl.
*G06T 7/70* (2017.01)
*A61B 1/267* (2006.01)
(Continued)

(52) U.S. Cl.
CPC .............. *G06T 7/70* (2017.01); *A61B 1/2676* (2013.01); *A61B 6/12* (2013.01); *G06N 3/04* (2013.01); *G06T 7/33* (2017.01); *G06T 7/55* (2017.01); *G16H 30/40* (2018.01); *G16H 50/50* (2018.01); *A61B 2090/3762* (2016.02); *G06T 2207/10016* (2013.01); *G06T 2207/10028* (2013.01); *G06T 2207/10068* (2013.01); *G06T 2207/10081* (2013.01); *G06T 2207/20081* (2013.01); *G06T 2207/20084* (2013.01); *G06T 2207/30244* (2013.01)

(58) Field of Classification Search
CPC ............ A61B 1/2676; A61B 2034/105; A61B 2090/376; A61B 2090/3762; G06N 3/0464; G06T 2207/10016; G06T 2207/10028; G06T 2207/10068; G06T 2207/10081; G06T 2207/20081; G06T 2207/20084; G06T 2207/30244; G06T 7/33; G06T 7/55; G06T 7/70
See application file for complete search history.

(56) References Cited

U.S. PATENT DOCUMENTS 7,388,583 B2 * 6/2008 Redert .................... G06T 15/10
                                                         348/51
10,270,962 B1 * 4/2019 Stout ................ G06V 30/19173
(Continued)

FOREIGN PATENT DOCUMENTS

WO    2020102584 A2    5/2020

OTHER PUBLICATIONS

Brachmann, E., Krull, A., Nowozin, S., Shotton, J., Michel, F., Gumhold, S., Rother, C., Dsac-differentiable ransac for camera localization, 2017, 11 pages.
(Continued)

*Primary Examiner* — Peter D Le
(74) *Attorney, Agent, or Firm* — Chang and Hale LLP

(57) ABSTRACT

Methods and systems provide improved navigation through tubular networks such as lung airways by providing improved estimation of location and orientation information of a medical instrument (e.g., an endoscope) within the tubular network. Various input data such as image data and CT data, are used to model the tubular networks, and the model information is used to generate a camera pose representing a specific site location within the tubular network and/or to determine navigation information including position and orientation for the medical instrument.

29 Claims, 16 Drawing Sheets

(51) Int. Cl.
*A61B 6/12* (2006.01)
*G06N 3/04* (2023.01)
*G06T 7/33* (2017.01)
*G06T 7/55* (2017.01)
*G16H 30/40* (2018.01)
*G16H 50/50* (2018.01)
*A61B 90/00* (2016.01)

(56) References Cited

U.S. PATENT DOCUMENTS

| | | | | |
|---|---|---|---|---|
| 10,380,753 | B1* | 8/2019 | Csordás | G06T 7/33 |
| 11,069,150 | B2* | 7/2021 | Sminchisescu | G06T 17/20 |
| 11,191,423 | B1* | 12/2021 | Zingaretti | G06T 7/0012 |
| 11,295,460 | B1* | 4/2022 | Aghdasi | G06T 19/20 |
| 2005/0129305 | A1* | 6/2005 | Chen | G06T 7/596 |
| | | | | 382/154 |
| 2007/0013710 | A1* | 1/2007 | Higgins | G06V 20/653 |
| | | | | 345/581 |
| 2007/0161854 | A1* | 7/2007 | Alamaro | A61B 1/00194 |
| | | | | 600/109 |
| 2009/0088897 | A1* | 4/2009 | Zhao | A61B 34/30 |
| | | | | 700/250 |
| 2010/0280365 | A1 | 11/2010 | Higgins et al. | |
| 2011/0043604 | A1* | 2/2011 | Peleg | G06T 3/4038 |
| | | | | 348/E7.001 |
| 2012/0056986 | A1* | 3/2012 | Popovic | A61B 1/04 |
| | | | | 348/45 |
| 2012/0069167 | A1* | 3/2012 | Liu | G06T 7/33 |
| | | | | 382/218 |
| 2012/0310098 | A1* | 12/2012 | Popovic | A61B 5/1077 |
| | | | | 600/476 |
| 2013/0259315 | A1* | 10/2013 | Angot | G06T 7/12 |
| | | | | 382/128 |
| 2013/0303883 | A1* | 11/2013 | Zehavi | A61B 6/5247 |
| | | | | 600/417 |
| 2013/0322717 | A1* | 12/2013 | Bar-Shalev | G06T 7/74 |
| | | | | 382/131 |
| 2014/0320629 | A1* | 10/2014 | Chizeck | G06T 15/04 |
| | | | | 348/81 |
| 2015/0235408 | A1* | 8/2015 | Gross | H04N 13/122 |
| | | | | 345/419 |
| 2015/0381908 | A1* | 12/2015 | De Bruijn | G02B 27/141 |
| | | | | 348/253 |
| 2016/0278721 | A1* | 9/2016 | Im | A61B 6/466 |
| 2017/0046833 | A1* | 2/2017 | Lurie | G06T 7/579 |
| 2017/0084006 | A1* | 3/2017 | Stewart | G06T 5/002 |
| 2017/0084027 | A1 | 3/2017 | Mintz et al. | |
| 2018/0174311 | A1* | 6/2018 | Kluckner | G06V 10/421 |
| 2019/0015163 | A1* | 1/2019 | Abhari | H04N 7/181 |
| 2019/0060013 | A1* | 2/2019 | McDowall | G02B 23/2415 |
| 2019/0087987 | A1* | 3/2019 | Bae | A61B 6/032 |
| 2019/0279383 | A1* | 9/2019 | Angelova | G06N 3/044 |
| 2020/0046436 | A1 | 2/2020 | Tzeisler et al. | |
| 2020/0051258 | A1* | 2/2020 | Miao | G06V 20/653 |
| 2020/0281454 | A1* | 9/2020 | Refai | A61B 1/00193 |
| 2021/0090226 | A1 | 3/2021 | Rauniyar et al. | |
| 2021/0097662 | A1* | 4/2021 | Wang | G06N 3/045 |
| 2021/0186619 | A1* | 6/2021 | Levi | A61B 34/10 |
| 2021/0280312 | A1* | 9/2021 | Freedman | G06V 10/764 |
| 2021/0406596 | A1* | 12/2021 | Hoffman | G06F 18/214 |
| 2022/0074994 | A1* | 3/2022 | Senn | G06N 7/01 |
| 2022/0076808 | A1* | 3/2022 | Vija | A61B 6/542 |
| 2022/0113804 | A1* | 4/2022 | Crowther | G09B 5/02 |
| 2022/0198693 | A1* | 6/2022 | Li | G06T 7/70 |
| 2022/0230384 | A1* | 7/2022 | Shin | G06T 15/506 |
| 2022/0249168 | A1* | 8/2022 | Besier | A61B 5/7275 |
| 2022/0257978 | A1* | 8/2022 | Kamen | A61N 5/1039 |
| 2022/0262023 | A1* | 8/2022 | Vignard | G06V 10/82 |
| 2022/0387129 | A1* | 12/2022 | Kinrot | A61B 6/5247 |
| 2023/0290042 | A1* | 9/2023 | Casella | G11B 27/031 |
| | | | | 345/427 |

OTHER PUBLICATIONS

Deligianni, F., Chung, A., Yang, G.Z., Patient-specific bronchoscope simulation with pqspace-based 2D/3D registration, Jan. 6, 2010, 13 pages.

Goodfellow, I.J., Pouget-Abadie, J., Mirza, M., Xu, B., Warde-Farley, D., Ozair, S., Courville, A.C., Bengio, Y., Generative Adversarial Nets, 2014, 9 pages.

He, K., Zhang, X., Ren, S., Sun, J., Deep residual learning for image recognition, 2016, 9 pages.

Jun-Yan Zhu, Taesung Park, Phillip Isola, Alexei A. Efros, Unpaired Image-to-Image Translation using Cycle-Consistent Adversarial Networks, 2017, 10 pages.

Luo, X., Feurestein, M., Deguchi, D., Kitasaka, T., Takabatake, H., Mori, K., Development and comparison of new hybrid motion tracking for bronchoscopic navigation, 2012, 22 pages.

Rai, L., Helferty, J.P., Higgines, W.E., Combined video tracking and image-video registration for continuous bronchoscopic guidance, 2008, 15 pages.

Shen, M., Gu, Y., Liu, N., Yang, G.Z., Context-Aware Depth and Pose Estimation for Bronchoscopic Navigation, Jan. 2019, 8 pages.

International Search Report for Appl. No. PCT/IB2022/052730, dated Jun. 22, 2022, 3 pages.

Written Opinion for Appl. No. PCT/IB2022/052730, dated Jun. 22, 2022, 3 pages.

International Preliminary Report on Patentability for Appl. No. PCT/IB2022/052730, dated Oct. 3, 2023, 4 pages.

* cited by examiner

VISION-BASED 6DOF CAMERA POSE ESTIMATION IN BRONCHOSCOPY

BACKGROUND

Field

The present disclosure relates generally to systems and methods for navigation and tracking of medical instruments, and more particularly to image-based detection and localization for navigation of instruments within a luminal network.

Description of Related Art

Medical procedures such as endoscopy (e.g., bronchoscopy) may involve accessing and visualizing the inside of a patient's lumen (e.g., airways) for diagnostic and/or therapeutic purposes. During a procedure, a flexible tubular tool or instrument, such as an endoscope, may be inserted into the patient's body. In some instances a second instrument can be passed through the endoscope to a tissue site identified for diagnosis and/or treatment.

Bronchoscopy is a medical procedure that allows a physician to examine the inside conditions of airways in a patient's lungs, such as bronchi and bronchioles. During the medical procedure, a thin, flexible tubular tool or instrument, known as a bronchoscope, may be inserted into the patient's mouth and passed down the patient's throat into his or her lung airways towards a tissue site identified for subsequent diagnosis and treatment. The bronchoscope can have an interior lumen (a "working channel") providing a pathway to the tissue site, and catheters and various medical tools can be inserted through the working channel to the tissue site.

In some medical procedures, human operator-controlled or robotically-enabled systems may be used to control the insertion and/or manipulation of the instruments used. The robotically-enabled medical system may include at least one robotic arm or other instrument positioning device including a manipulator assembly used to control the positioning of the instrument during the procedures.

SUMMARY

A robotically-enabled medical system can be configured for tracking and navigation of an instrument during a medical or surgical procedure. The system can be used to perform a variety of procedures, including both minimally invasive procedures (e.g., laparoscopy) and non-invasive procedures (e.g., endoscopy). Among endoscopic procedures, the system can be used to perform bronchoscopy, ureteroscopy, gastroenterology, etc. During such procedures, a physician can guide an instrument through a luminal network of a patient. The luminal network can include a plurality of branched lumens (such as in bronchial or renal networks), or a single lumen (such as a gastrointestinal tract).

The robotically-enabled medical system can include a localization system (also referred to as a navigation system) for locating and/or guiding the medical instrument within the luminal network. In some embodiments, the localization system can determine or estimate a position and/or orientation of the instrument within the luminal network. The localization system may receive and process various types of location or position data to determine the instrument's position and/or orientation. For example, the localization system can process image data, electromagnetic (EM) data, kinematic data, inertial measurement data, shape sensing data, or the like to determine the instrument's position. The localization system may derive or estimate the instrument's position from one or a combination of these data inputs.

For instance, the localization system may use a combination of data inputs that includes EM data generated from EM sensors on the instrument to determine the instrument's position and orientation, as the instrument moves through the luminal network. Navigation based on EM data can provide real-time six degrees of freedom (6 DoF) pose of the instrument tip regardless of the image quality of the camera. However, the accuracy of EM navigation and tracking depends on a good initial registration between the EM field coordinate system and an associated coordinate system, such as a computed tomography (CT) coordinate system derived from pre-operative CT images. Furthermore, EM readings can be noisy and distorted due to ferromagnetic inference caused by metal instruments and CT scanners in the operating room. Moreover, the accuracy of an instrument pose estimated by EM tracking can be compromised when a large effect of respiratory motion presents, especially at peripheral lumens (e.g., airways). Inaccurate instrument pose estimation can cause issues such as depth mismatch, incorrect roll in the virtual luminal view, or navigation failure. When this occurs, the determined position and/or orientation of the instrument may not be reliable due to the EM data inputs used by the localization system. If the determined position is being displayed to the physician, the physician may perceive inaccuracies in position and/or orientation as the localization system attempts to determine the position and orientation.

The tracking and navigation methods and systems described herein can be used, for example, to reduce, mitigate, or eliminate the shortcomings in EM-based localization. This may be accomplished by, in one example, a vision-based approach to estimate 6 DoF camera poses in the CT space, based on video image data and one or more luminal models determined at least in part from pre-operative CT scans. A first model that characterizes the luminal structures can be determined at least in part from video images of visible lumens. A plurality of second models can be generated at least in part from the CT scans. A candidate model from the plurality of second models that has the highest similarity of shape to the first model can be used to generate a localization camera pose showing position and orientation of the instrument within the lumen. This camera pose can provide an improved experience for the physician, allowing for improved control of the robotically-enabled medical systems.

The described systems, devices, and methods used to determine or estimate the position of an instrument within the luminal network can also facilitate the identification and tracking of various anatomical features based on images of such features obtained using a scope device or other medical instrument. Such feature identification and/or tracking can facilitate the targeting of certain anatomical features in connection with a medical procedure, such as bronchoscopy or other procedure accessing the bronchial anatomy, for example. The systems, methods and devices of this disclosure each have several innovative aspects, no single one of which is solely responsible for the desirable attributes disclosed herein.

In one aspect, the present disclosure relates to a method of generating a camera pose representative of a spatial location within an internal anatomical structure. The method comprises determining a first depth map that characterizes an internal anatomical structure based at least in part on image data representing the internal anatomical structure, generating a plurality of second depth maps based at least in part on computed tomography (CT) image data, each of the second depth maps representing a virtual model of the internal anatomical structure, identifying one of the plurality of second depth maps that has a highest similarity of shape to the first depth map, and generating a camera pose based at least in part on the identified one of the plurality of second depth maps.

The method can further comprise determining the first depth map from video image data using a convolutional neural network (CNN). In another embodiment, the method further comprises estimating camera pose parameters by solving a transformation matrix between a 3D point cloud of the virtual model of the internal anatomical structure and a point cloud inverse projected from the first depth map. In one example, a convolutional neural network (CNN) is employed to solve the transformation matrix and estimate the camera pose parameters. In another example, estimating camera pose parameters further comprises identifying a desired location in the one of the plurality of second depth maps that corresponds to a location in one or more video images, using the first depth map.

In some embodiments, generating the plurality of second depth maps and identifying one of the plurality of second depth maps that represents the desired location is an iterative or continuous process. For example, the iterative process can include using one of the plurality of second depth maps of a previous iteration to initialize generating the plurality of second depth maps. In other embodiments, the method further comprises generating the plurality of second depth maps using a plurality of virtual camera poses.

In an embodiment, the camera pose comprises a virtual spatial estimation representative of a physical spatial location within the internal anatomical structure. In the embodiment, the method may further comprise defining the camera pose in coordinates relative to the CT image data.

In another aspect, the present disclosure relates to a method of generating a camera pose representative of a spatial location within a bronchial airway. The method comprises determining a first depth map that characterizes an internal anatomical shape structure of a bronchial airway based at least in part on video image data representing the internal anatomical shape structure of the bronchial airway, generating a virtual camera pose representing an estimated location and orientation within the bronchial airway from computed tomography (CT) image data representing the internal anatomical shape structure of the bronchial airway, generating a plurality of second depth maps based at least in part on the virtual camera pose, each of the second depth maps representing a virtual model of the internal anatomical shape structure of the bronchial airway, identifying one of the plurality of second depth maps that has a highest similarity of shape to the first depth map, and generating a camera pose representing a location and an orientation having six-degrees of freedom (6 DoF) within the bronchial airway, based at least in part on the identified one of the plurality of second depth maps.

The method can further comprise forming the first depth map using the video image data with a convolutional neural network (CNN) that performs domain adaptation. In one example, the method may further include learning a mapping function by the CNN with supervised learning by pairing video image data to corresponding first depth maps, where the first depth maps are formed as a function of the video image data. In another example, the method may further include learning a mapping function by the CNN with unsupervised generative adversarial learning with a cyclic consistency that does not require paired data, where the first depth map is formed as a function of the video image data.

In an embodiment, the method further comprises pre-computing a dataset comprised of paired second depth maps and virtual camera poses, relative to the first depth map. In an example, the method may further comprise applying image registration techniques to find a candidate second depth map relative to the dataset with a highest similarity of shape to the first depth map. In one embodiment, the method includes using a virtual camera pose value of the candidate second depth map as the camera pose or as an initial value for a candidate virtual camera pose for iteratively generating a next plurality of second depth maps. In another embodiment, the method includes estimating a relative pose between the candidate second depth map and the first depth map by passing the candidate second depth map and the first depth map into a spatial transformation network configured to regress a relative transformation between the candidate second depth map and the first depth map.

In another aspect, the present disclosure relates to a medical system. The medical system comprises a medical instrument having a camera associated with a distal end thereof and control circuitry communicatively coupled to the medical instrument. In an embodiment, the control circuitry is configured to generate image data of an internal anatomical structure, determine a first depth map that characterizes the internal anatomical structure based at least in part on the image data, generate a virtual camera pose representing an estimated location and an orientation within the internal anatomical structure based at least in part on computed tomography (CT) image data of the internal anatomical structure, generate a plurality of second depth maps based at least in part on the virtual camera pose, each of the second depth maps representing a virtual model of the internal anatomical structure, identify one the plurality of second depth maps that has a highest similarity of shape to the first depth map, and generate a camera pose representing a location and an orientation having six-degrees of freedom (6 DoF) within the internal anatomical structure, based at least in part on the identified one of the plurality of second depth maps.

In an embodiment, the control circuitry is further configured to represent the first depth map with a first point cloud and a second depth map with a second point cloud. The control circuitry can be further configured to determine deep geometric features based at least in part on the first and second point clouds using a first neural network. Additionally or alternately the control circuitry can be further configured to establish a point-wise correspondence between a plurality of key points of the first point cloud and an associated plurality of key points of the second point cloud.

In an example, the control circuitry is further configured to establish the point-wise correspondence by searching in a shared feature space using a second neural network, the shared feature space relative to the deep geometric features. In another example, the control circuitry is further configured to pass the point-wise correspondence into another network to output a second point-wise correspondence. In one embodiment, the other network comprises a differentiable random sample consensus (RANSAC) network. The control circuitry can be further configured to generate the camera pose based at least in part on the second point-wise correspondence.

In a further aspect, the present disclosure relates to a medical system. The medical system comprises a means for determining a first depth map that characterizes an internal anatomical structure based at least in part on image data representing the internal anatomical structure, a means for generating a plurality of second depth maps based at least in part on computed tomography (CT) image data, each of the second depth maps representing a virtual model of the internal anatomical structure, a means for identifying one of the plurality of second depth maps that has a highest similarity of shape to the first depth map, and a means for generating a camera pose based at least in part on the identified one of the plurality of second depth maps.

In various embodiments, the medical system includes an additional means for forming the camera pose using at least one of electromagnetic (EM) data, kinematic data, inertial measurement data, or shape sensing data. The medical system can also include a means for computing the camera pose in real time, relative to the internal anatomical structure. For example, the internal anatomical structure can be intermittently in motion.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 7-1 and 7-2 illustrate an example instrument driver.

DETAILED DESCRIPTION

1. Overview

Figure 1:
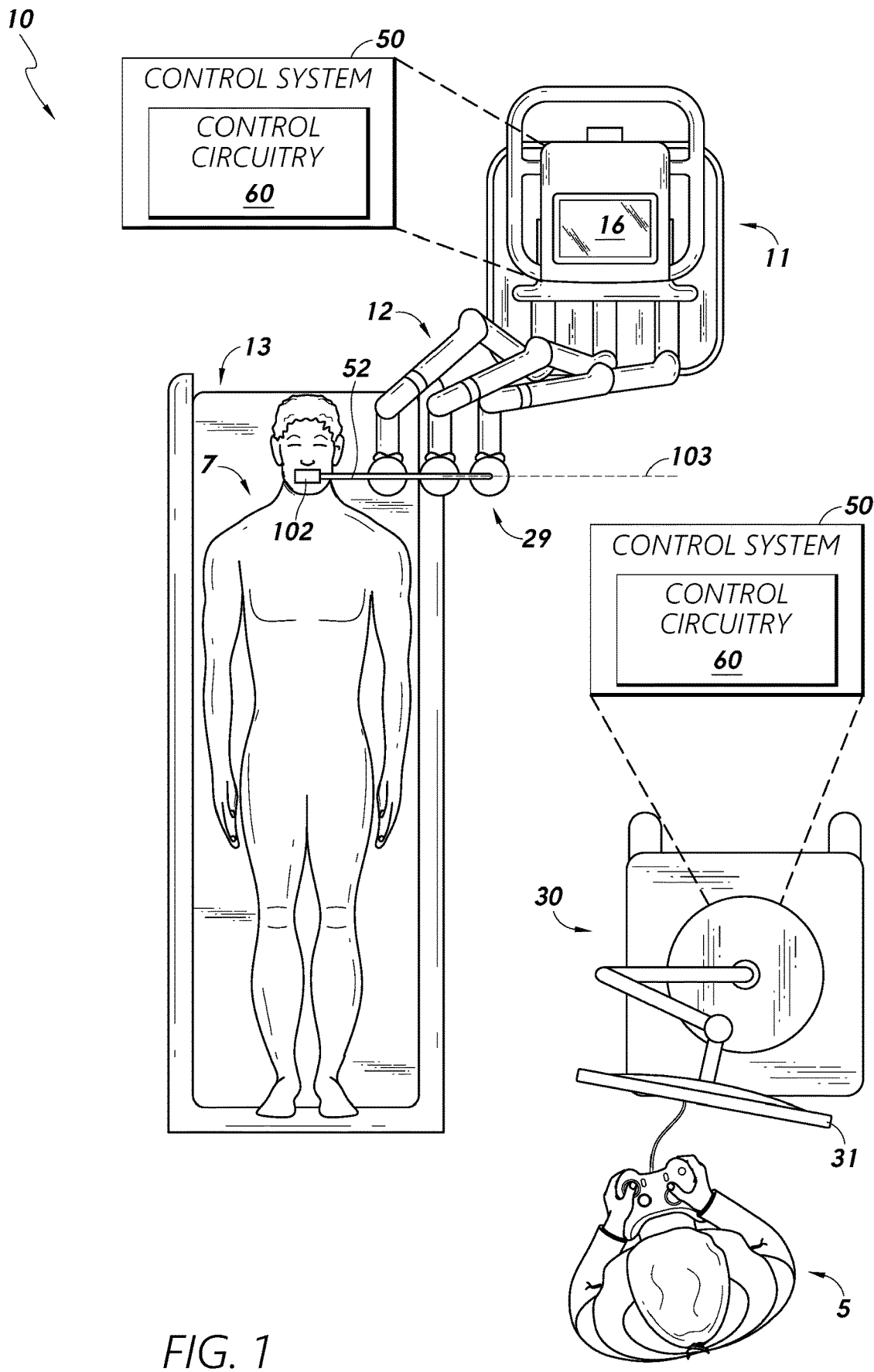
FIG. 1 illustrates an embodiment of a cart-based robotic system arranged for diagnostic and/or therapeutic bronchoscopy procedure(s).

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroenterology, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

The terms "scope" and "endoscope" are used herein according to their broad and ordinary meanings, and may refer to any type of elongate medical instrument having image generating, viewing, and/or capturing functionality and configured to be introduced into any type of organ, cavity, lumen, chamber, or space of a body. For example, references herein to scopes or endoscopes may refer to a bronchoscope, ureteroscope, cystoscope, nephroscope, arthroscope, colonoscope, laparoscope, borescope, or the like. Scopes/endoscopes, in some instances, may comprise a rigid or flexible tube, and may be dimensioned to be passed within an outer sheath, catheter, introducer, or other lumen-type device, or may be used without such devices.

Robotic-assisted percutaneous procedures can be implemented in connection with various medical procedures, such as bronchial procedures, wherein robotic tools can enable a physician to perform endoscopic target access (e.g., bronchoscope) as well as percutaneous access or/treatment. However, movements of target anatomical features during operation can be problematic in cases where the operating physician relies on a fixed percutaneous access target position. Advantageously, aspects of the present disclosure relate to real-time target tracking/guidance in medical procedures, which may also be utilized by the operating physician to direct a percutandeous-access instrument (e.g., needle or other rigid tool) and/or to guide robotic instrumentation, such as by adjusting endoscope position and/or alignment automatically in response to such real-time target-tracking information. To facilitate such functionality, embodiments of the present disclosure may advantageously provide mechanisms for automatic target detection, tracking, and/or three-dimensional positioned estimation to assist physicians during various surgical operations. Although aspects of the present disclosure are described herein for convenience in the context of bronchoscope-guided procedures, it should be understood that inventive aspects of the present disclosure may be implemented in any suitable or desirable type of percutaneous and/or endoscopic medical procedure, whether robotic or not.

A. Robotic System—Cart

Figure 2:
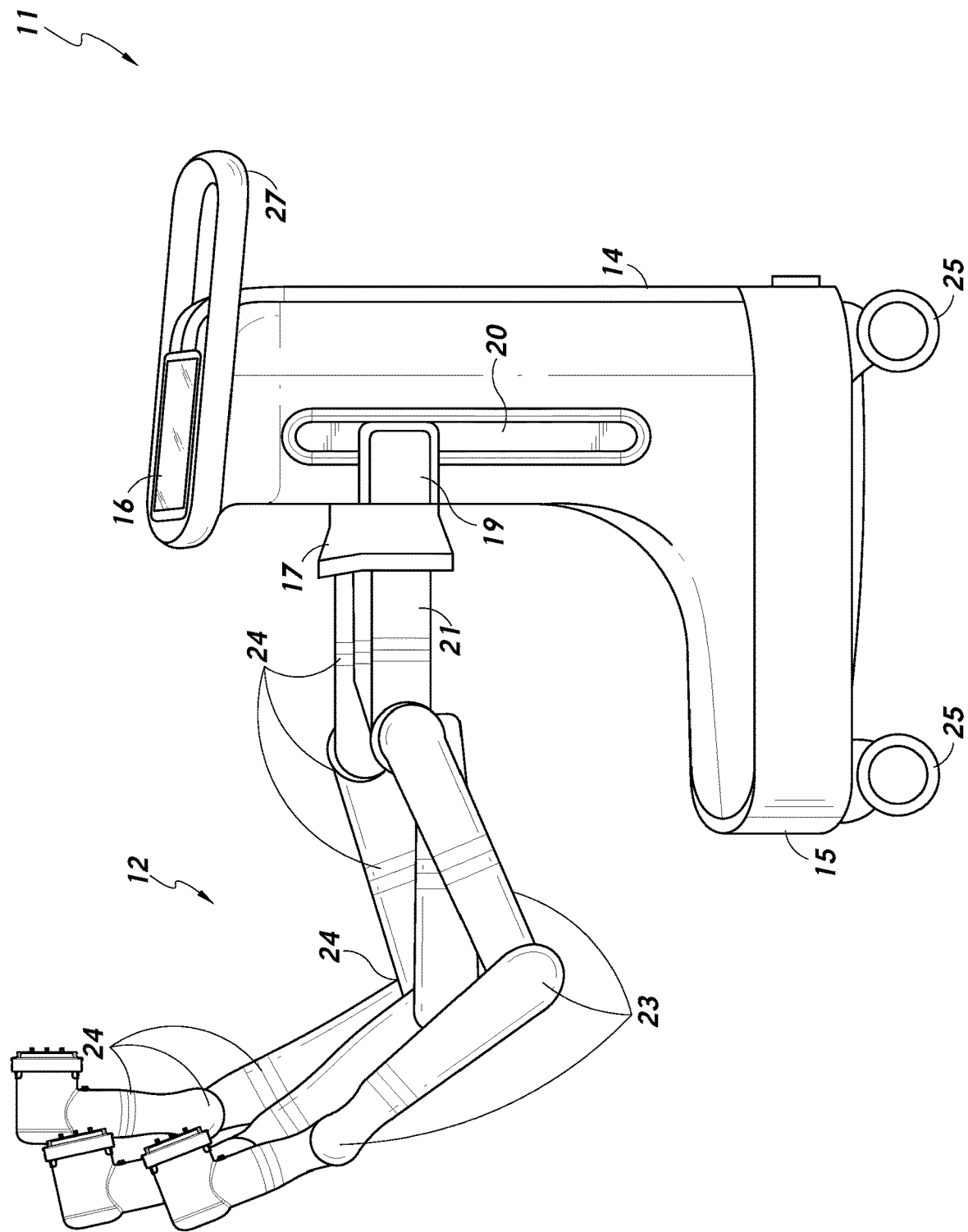
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 52, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope 52 for GI procedures. FIG. 2 depicts an example embodiment of the cart in greater detail.

With continued reference to FIG. 1, once the cart 11 is properly positioned, the robotic arms 12 may insert the steerable endoscope 52 into the patient robotically, manually, or a combination thereof. As shown, the steerable endoscope 52 may comprise at least two telescoping parts, such as an inner leader portion and an outer sheath portion, each portion coupled to a separate instrument driver 86 from the set of instrument drivers, each instrument driver 86 coupled to the distal end of an individual robotic arm 12. This linear arrangement of the instrument drivers 86, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 86 along the virtual rail 29 telescopes the inner leader portion relative to the outer sheath portion or advances or retracts the endoscope 52 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 52 while minimizing friction that results from bending the endoscope 52 into the patient's mouth.

The endoscope 52 may be directed down the patient's trachea and lungs after insertion using precise commands from the robotic system until reaching the target destination or operative site. In order to enhance navigation through the patient's lung network and/or reach the desired target, the endoscope 52 may be manipulated to telescopically extend the inner leader portion from the outer sheath portion to obtain enhanced articulation and greater bend radius. The use of separate instrument drivers 86 also allows the leader portion and sheath portion to be driven independent of each other.

For example, the endoscope 52 may be directed to deliver a biopsy needle to a target, such as, for example, a lesion or nodule within the lungs of a patient. The needle may be deployed down a working channel that runs the length of the endoscope 52 to obtain a tissue sample to be analyzed by a pathologist. Depending on the pathology results, additional tools may be deployed down the working channel of the endoscope 52 for additional biopsies. After identifying a nodule to be malignant, the endoscope 52 may endoscopically deliver tools to resect the potentially cancerous tissue. In some instances, diagnostic and therapeutic treatments may need to be delivered in separate procedures. In those circumstances, the endoscope 52 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician 5 and his/her staff. Additionally, the division of functionality between the cart/table and the support tower 30 reduces operating room clutter and facilitates improving clinical workflow. While the cart 11 may be positioned close to the patient 7, the tower 30 may be stowed in a remote location to stay out of the way during a procedure.

In support of the robotic systems described above, the tower 30 may include component(s) of a computer-based control system 50 that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system 10 to actuate the relevant carriages and arm mounts, actuate the robotics arms, and control the medical instruments. For example, in response to receiving the control signal, the motors in the joints of the robotics arms 12 may position the arms 12 into a certain posture.

The tower 30 may also include a pump, flow meter, valve control, and/or fluid access in order to provide controlled irrigation and aspiration capabilities to system that may be deployed through the endoscope 52. These components may also be controlled using the control system 50 of tower 30. In some embodiments, irrigation and aspiration capabilities may be delivered directly to the endoscope 52 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system 50, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

Figure 8:
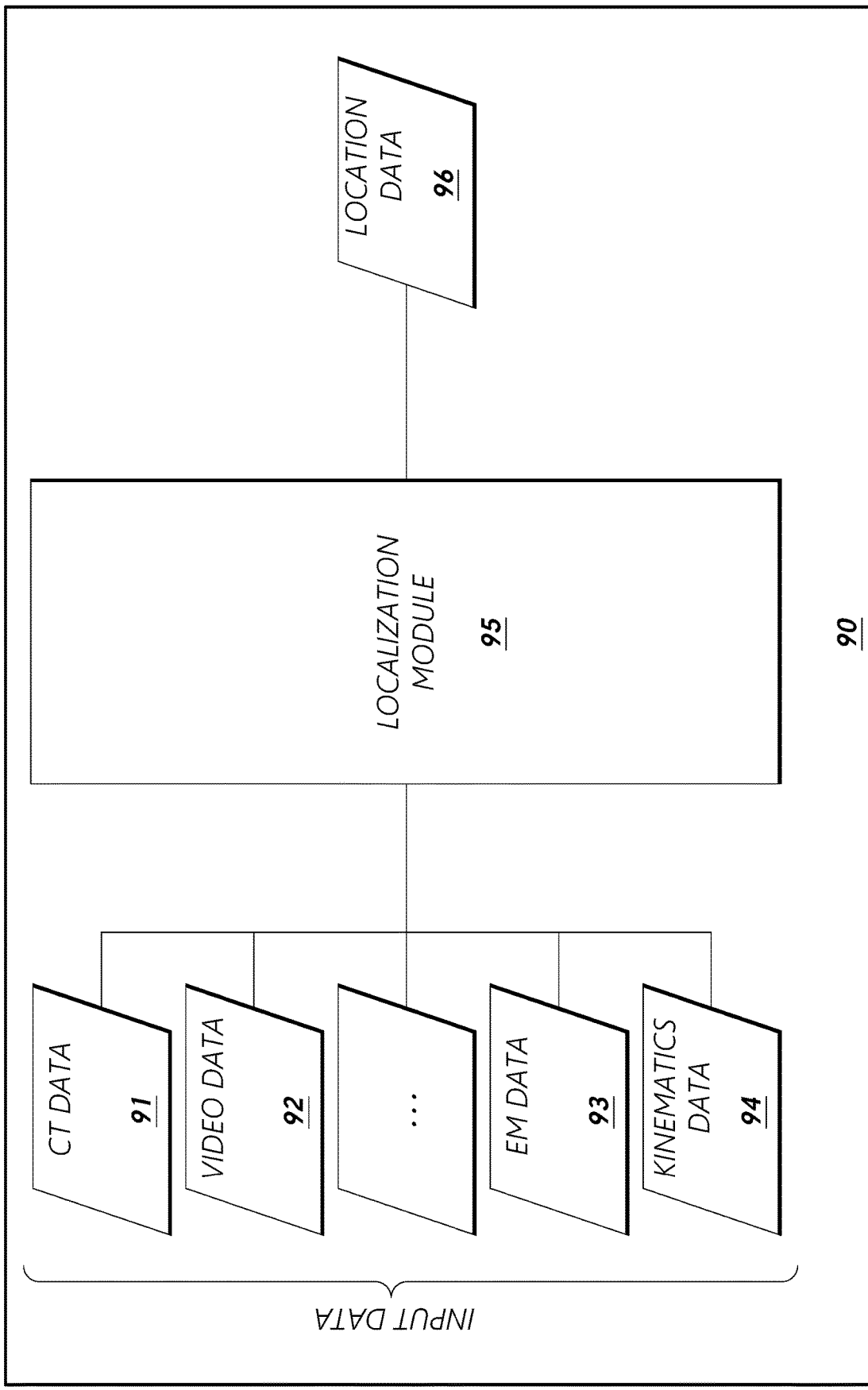
FIG. 8 depicts a block diagram illustrating a localization system that estimates a location of one or more elements of the robotic systems of FIGS. 1-7, such as the location of the instrument of FIG. 6, in accordance with an example embodiment.

The tower 30 may also include a console 31 in addition to other consoles available in the rest of the system, e.g., console mounted on top of the cart. The console 31 may include a user interface and a display screen, such as a touchscreen, for the physician operator. The displays may include electronic monitors (e.g., LCD displays, LED displays, touch-sensitive displays), virtual reality viewing devices (e.g., goggles or glasses), and/or other display devices. In some embodiments, one or more of the displays displays position information about the instrument, for example, as determined by the localization system 90 (FIG. 8). In some embodiments, one or more of the displays shows a preoperative model of the patient's luminal network 130. The positional information can be overlaid on the preoperative model. The displays can also display image information received from a camera (e.g., imaging device 315) or another sensing device positioned on the instrument within the luminal network 130. In some embodiments, a model or representation of the instrument is displayed with the preoperative model to help indicate a status of a surgical or medical procedure.

Consoles in system 10 are generally designed to provide both robotic controls as well as pre-operative and real-time information of the procedure, such as navigational and localization information of the endoscope 52. The operator may provide the inputs for controlling the robotic system 10, for example, to navigate or guide the instrument to an area of interest via the console 31. When the console 31 is not the only console available to the physician 5, it may be used by a second operator, such as a nurse, to monitor the health or vitals of the patient and the operation of system, as well as provide procedure-specific data, such as navigational and localization information. The console 31 may be embodied in a wide variety of arrangements or configurations. In the illustrated example, the console 31 includes a console base, displays (e.g., monitors), and one or more I/O controllers (e.g., keyboard, joystick, etc.). A user (e.g., the operator or physician) can remotely control the medical robotic system 10 (e.g., the systems described with reference to FIGS. 1-16) from a convenient position using the console 31.

The tower 30 may be coupled to the cart 11 and endoscope 52 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors (e.g., instrument driver) 75, separated by a series of linkages 23 that are connected by a series of joints 24, each joint comprising an independent actuator, each actuator comprising an independently controllable motor. Each independently controllable joint 24 represents an independent degree of freedom available to the robotic arm. Each of the arms 12 have seven joints 24, and thus provide seven degrees of freedom. A multitude of joints 24 result in a multitude of degrees of freedom, allowing for "redundant" degrees of freedom. Redundant degrees of freedom allow the robotic arms 12 to position their respective end effectors 75 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen) to provide the physician user with both pre-operative and intra-operative data. Potential pre-operative data on the touchscreen may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position the physician 5 may view the console 16, robotic arms 12, and patient while operating the console 16 from behind the cart 11. As shown, the console 16 also includes a handle 27 to assist with maneuvering and stabilizing cart 11.

Figure 3:
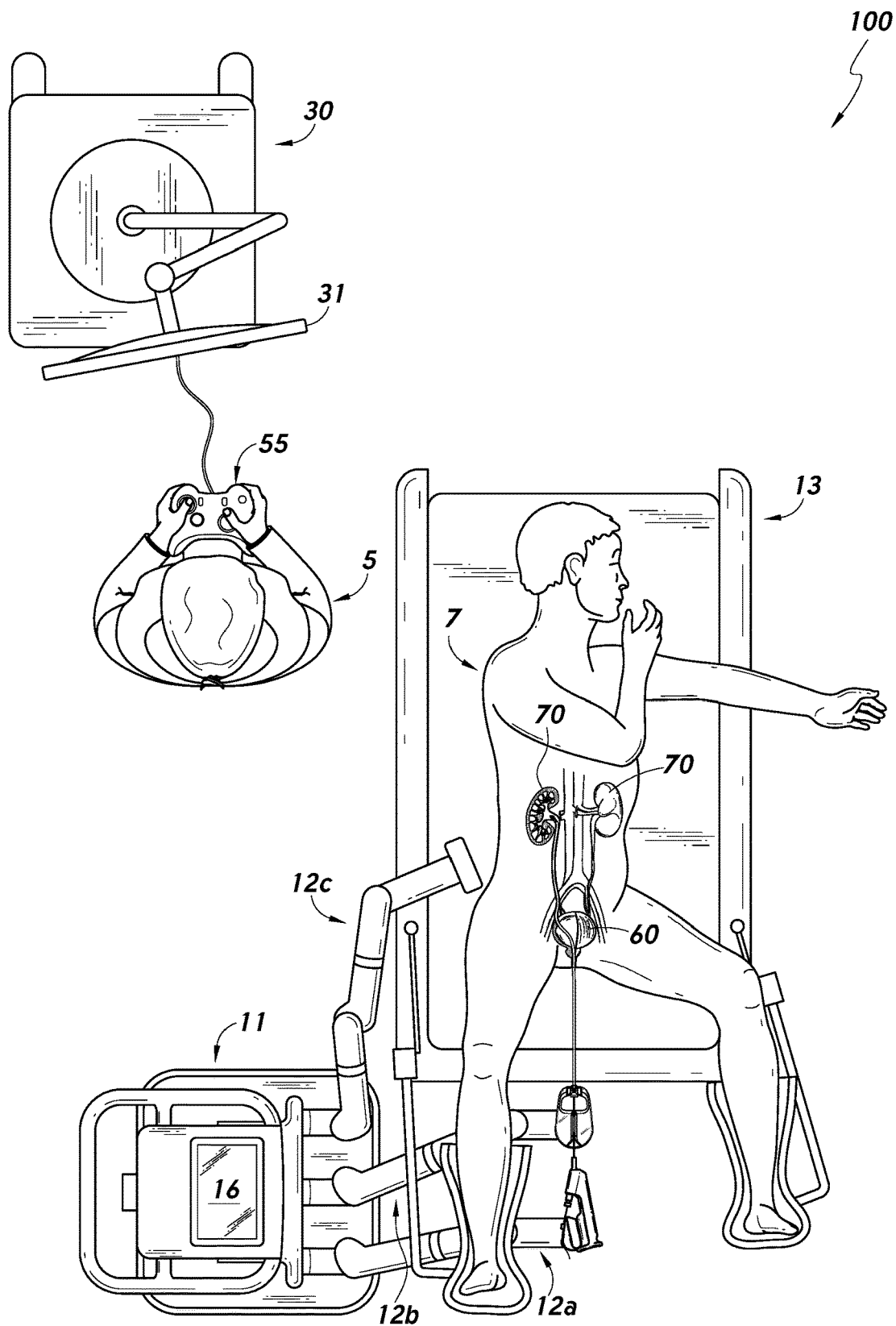
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope, a procedure-specific endoscope 52 designed to traverse a patient's urethra and ureter, to the lower abdominal area of the patient. In a ureteroscopy, it may be desirable for the ureteroscope to be directly aligned with the patient's urethra to reduce friction and forces on the sensitive anatomy in the area. As shown, the cart 11 may be aligned at the foot of the table to allow the robotic arms 12 to position the ureteroscope for direct linear access to the patient's urethra. From the foot of the table, the robotic arms 12 may insert ureteroscope along the virtual rail 29 directly into the patient's lower abdomen through the urethra.

After insertion into the urethra, using similar control techniques as in bronchoscopy, the ureteroscope may be navigated into the bladder 60, ureters, and/or kidneys 70 for diagnostic and/or therapeutic applications. For example, the ureteroscope may be directed into the ureter and kidneys 70 to break up kidney stone build up using laser or ultrasonic lithotripsy device deployed down the working channel of the ureteroscope. After lithotripsy is complete, the resulting stone fragments may be removed using baskets deployed down the ureteroscope.

Figure 4:
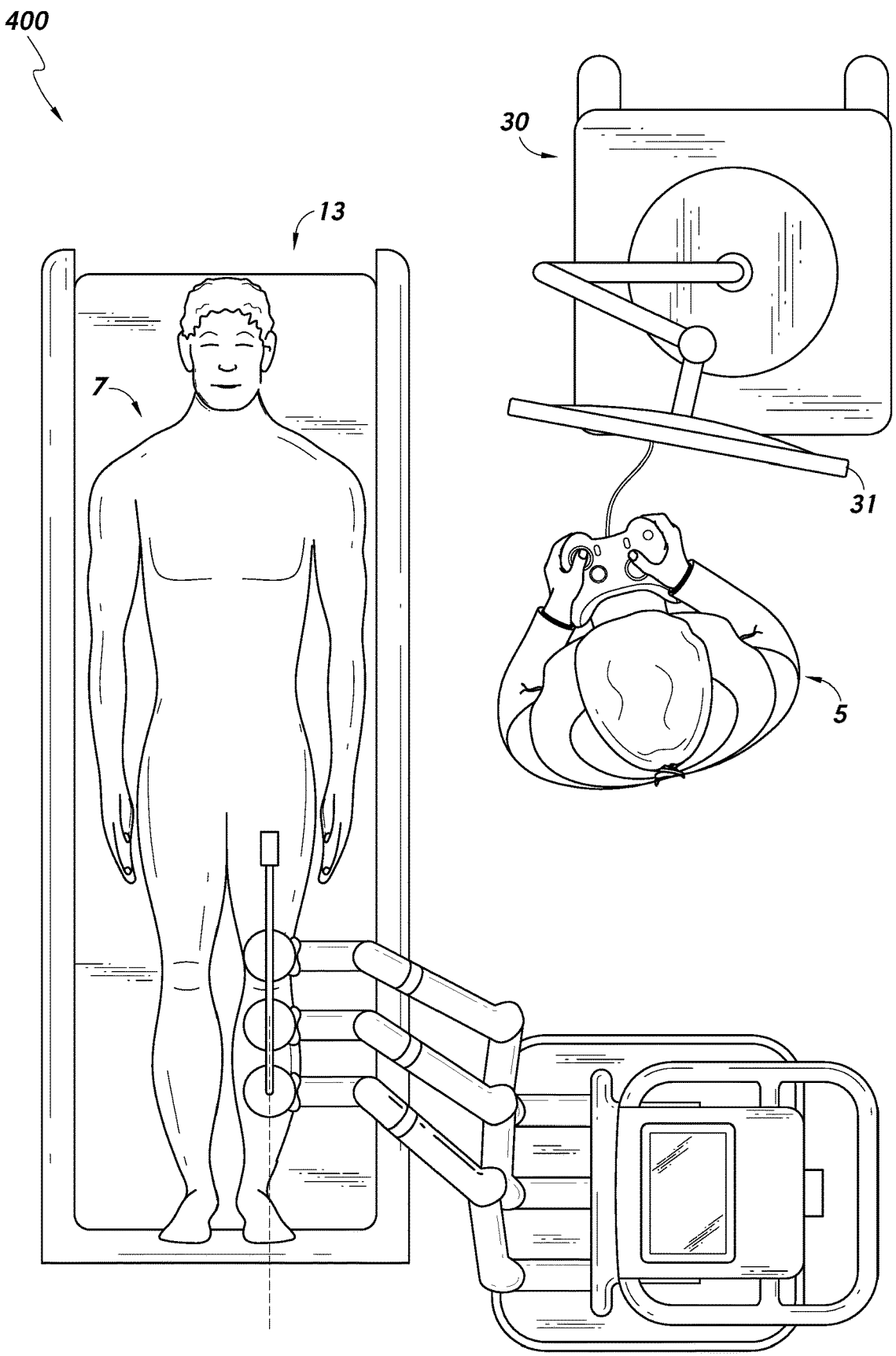
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such the cart 11 may deliver a medical instrument 34, such as a steerable catheter, to an access point in the femoral artery in the patient's leg. The femoral artery presents both a larger diameter for navigation as well as relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 29 with direct linear access to the femoral artery access point in the patient's thigh/hip region. After insertion into the artery, the medical instrument 34 may be directed and inserted by translating the instrument drivers 86. Alternatively, the cart 11 may be positioned around the patient's upper abdomen in order to reach alternative vascular access points, such as, for example, the carotid and brachial arteries near the shoulder and wrist.

B. Robotic System—Table

Figure 5:
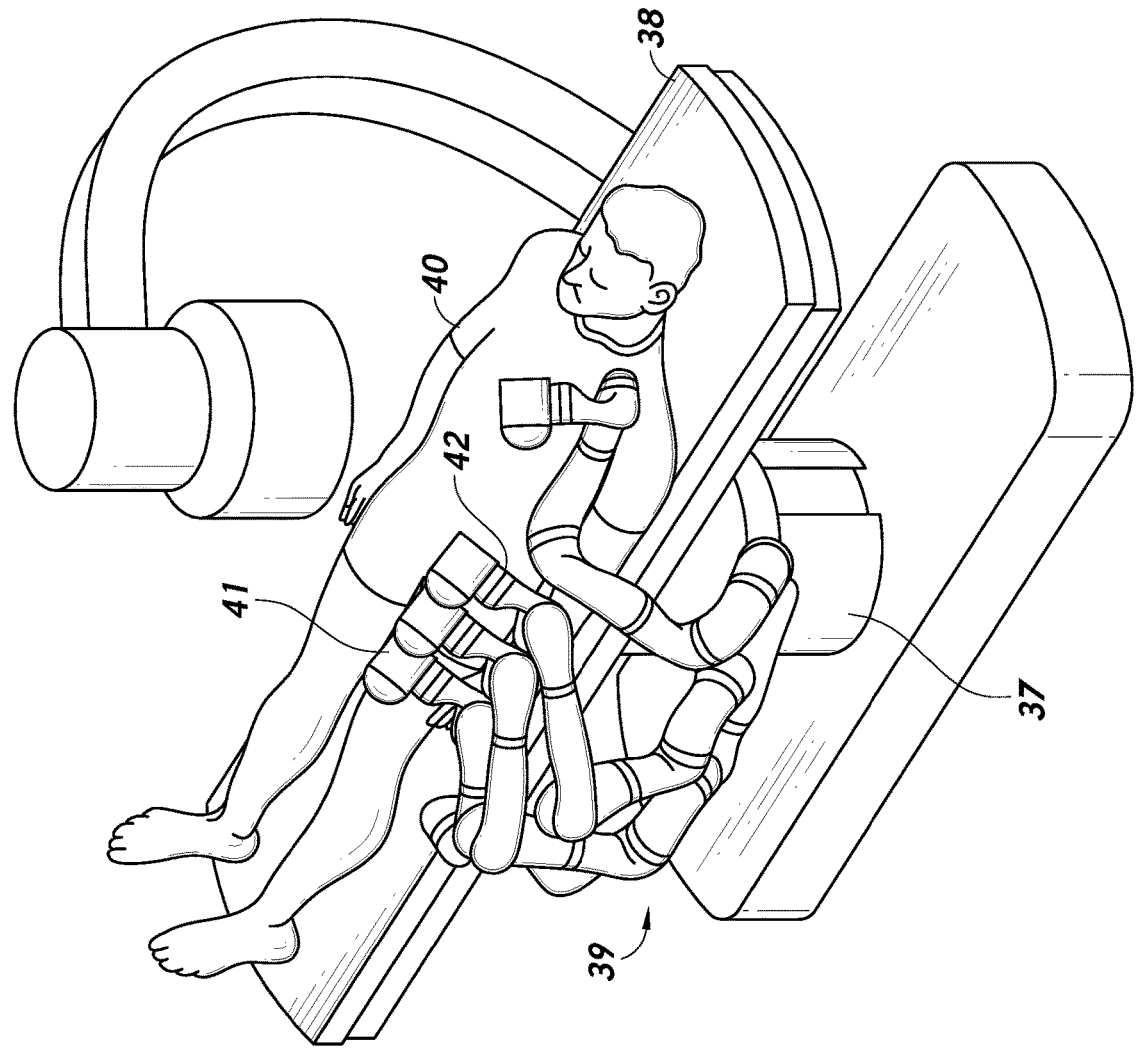
FIG. 5 illustrates an embodiment of a table-based robotic system arranged for an endoscopy procedure.

Embodiments of the robotically-enabled medical system 10 may also incorporate the patient's table 13. Incorporation of the table 13 reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

C. Instrument Driver & Interface

Figure 6:
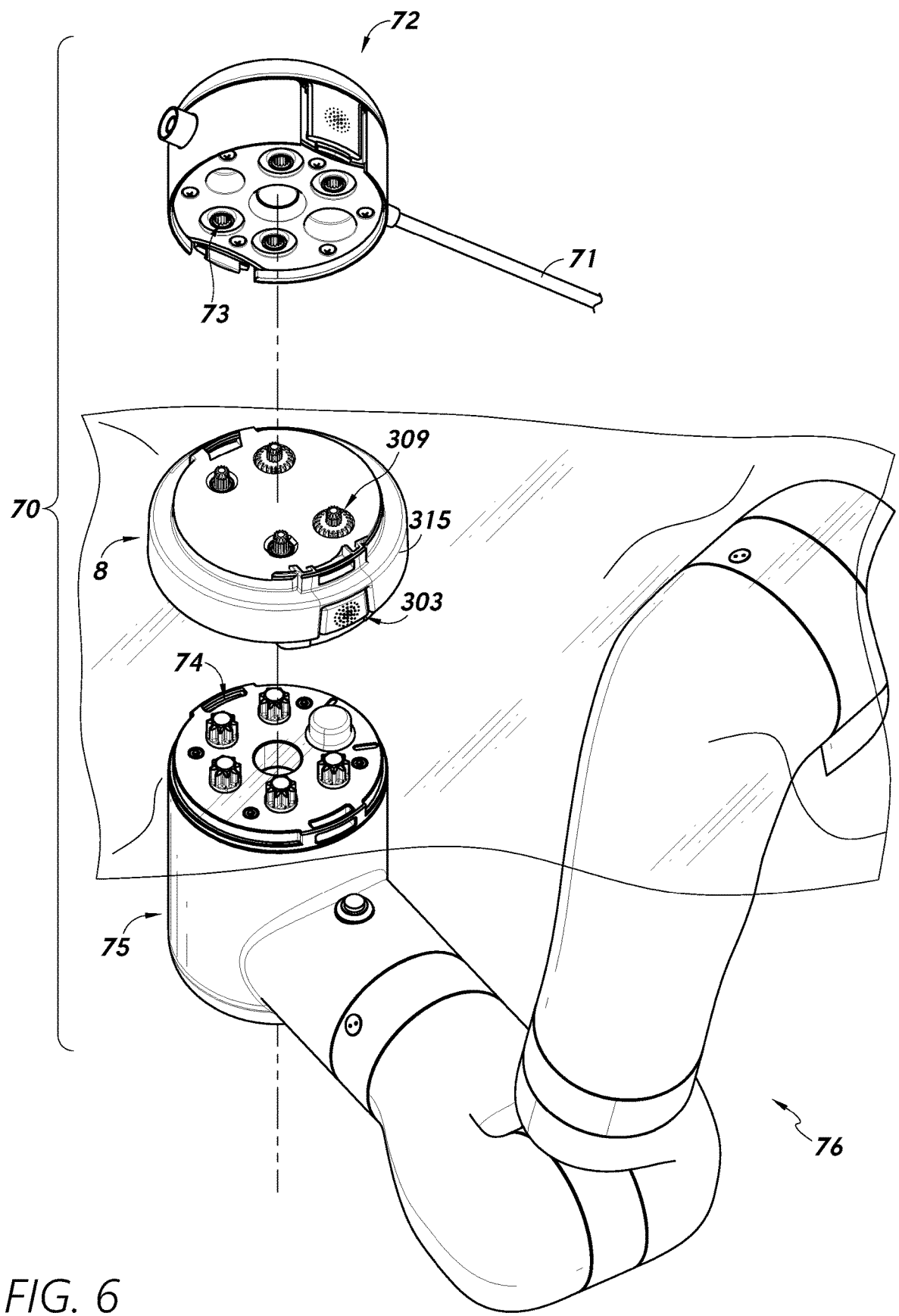
FIG. 6 illustrates an exemplary medical instrument with a paired instrument driver.

FIG. 6 shows an exploded view of an example instrument device manipulator assembly 70 associated with a robotic arm 76 in accordance with one or more embodiments. The instrument manipulator assembly 70 includes an instrument driver 75 (e.g., end effector) associated with a distal end of the robotic arm 76. The instrument manipulator assembly 70 further includes the instrument handle/base 72 associated with the catheter. The instrument handle 72 can incorporate electro-mechanical means for actuating the instrument shaft 71. In this example, the instrument is described as a catheter, but the instrument may be any type of medical/surgical instrument. Description herein of upward-facing and downward-facing surfaces, plates, faces, components, and/or other features or structures may be understood with reference to the particular orientation of the device manipulator assembly 70 shown in FIG. 6. That is, although the instrument driver 75 may generally be configurable to face and/or be oriented in a range of directions and orientations, for convenience, description of such components herein may be in the context of the generally vertical facing orientation of the instrument driver 75 shown in FIG. 6.

In some embodiments, the instrument device manipulator assembly 70 further includes an adapter 8 configured to provide a driver interface between the instrument driver 75 and the instrument handle 72. The adapter 8 and/or the instrument handle 72 may be removable or detachable from the robotic arm 76 and may be devoid of any electro-mechanical components, such as motors, in some embodiments. This dichotomy may be driven by the need to sterilize medical instruments used in medical procedures and/or the inability to adequately sterilize expensive capital equipment due to their intricate mechanical assemblies and sensitive electronics. Accordingly, the instrument handle 72 and/or adapter 8 may be designed to be detached, removed, and/or interchanged from the instrument driver 75 (and thus the system) for individual sterilization or disposal. In contrast, the instrument driver 75 need not be changed or sterilized in some cases and/or may be draped for protection.

The adapter 8 (sometimes referred to as "the sterile adapter 8") can include connectors to transfer pneumatic pressure, electrical power, electrical signals, mechanical actuation, and/or optical signals from the robotic arm 76 and/or instrument driver 75 to the instrument handle 72. For example, the adapter 8 can include a drive input assembly(s) to couple to a drive output assembly(s) of the end effector 75 and a drive output assembly(s) configured to couple to a drive input assembly(s) of the instrument handle 72. The drive input assembly and drive output assembly of the adapter 8 can be coupled together to transfer control/actuation from the instrument driver 75 to the instrument handle 72.

The instrument handle 72 may be configured to manipulate the catheter using one or more direct drives, harmonic drives, geared drives, belts and pulleys, magnetic drives, and/or other manipulator means or mechanisms. The robotic arm 76 can advance/insert or retract the coupled catheter into or out of the treatment site. In some embodiments, the instrument handle 72 can be removed and replaced with a different type of instrument handle, such as to manipulate a different type of instrument.

The end effector 75 (e.g., instrument driver) of the robotic arm 76 can include various components/elements configured to connect to and/or align with components of the adapter 8, handle 72, and/or catheter. For example, the end effector 75 can include the drive output assembly(s) (e.g., drive splines, gears, or rotatable disks with engagement features) to control/articulate a medical instrument, a reader to read data from a medical instrument (e.g., radio-frequency identification (RFID) reader to read a serial number from a medical instrument and/or other data/information), one or more fasteners 74 to attach the catheter and/or the adapter 8 to the instrument driver 75, and markers to align with an instrument that is manually attached to a patient (e.g., an access sheath) and/or to define a front surface of the device manipulator assembly 70. The one or more fasteners 74 can be configured to couple to one or more attachment mechanisms 303 of the adapter 8 and/or the one or more attachment mechanisms of the handle 72. In some embodiments, the end effector 75 and/or the robotic arm 76 includes a button to enable an admittance control mode, wherein the robotic arm 76 can be manually moved.

In some configurations, a sterile drape, such as a plastic sheet or the like, may be disposed between the instrument driver 75 and the adapter 8 to provide a sterile barrier between the robot arm 76 and the catheter. For example, the drape may be coupled to the adapter 8 in such a way as to allow for translation of mechanical torque from the driver 75 to the adapter 8. The adapter 8 may generally be configured to maintain a seal around the actuating components thereof, such that the adapter 8 provides a sterile barrier itself. The use of the drape coupled to the adapter 8 and/or more other component(s) of the device manipulator assembly 70 may provide a sterile barrier between the robotic arm 76 and the surgical field, thereby allowing for the use of a robotic system associated with the arm 76 in the sterile surgical field. The driver 75 may be configured to be coupled to various types of sterile adapters that may be loaded onto and/or removed from the driver 75 of the robotic arm 76. With the arm 76 draped in plastic, the physician and/or other technician(s) may interact with the arm 76 and/or other components of the robotic cart (e.g., screen) during a procedure. Draping may further protect against equipment biohazard contamination and/or minimize clean-up after procedure.

Although the particular adapter 8 shown in FIG. 6 may be configured for coupling with the catheter handle 72, such as an aspiration catheter handle, adapters for use with device manipulator assemblies in accordance with aspects of the present disclosure may be configured for coupling with any type of surgical or medical device or instrument, such as an endoscope (e.g., ureteroscope), basketing device, laser fiber driver, or the like.

Figures 2, 7:
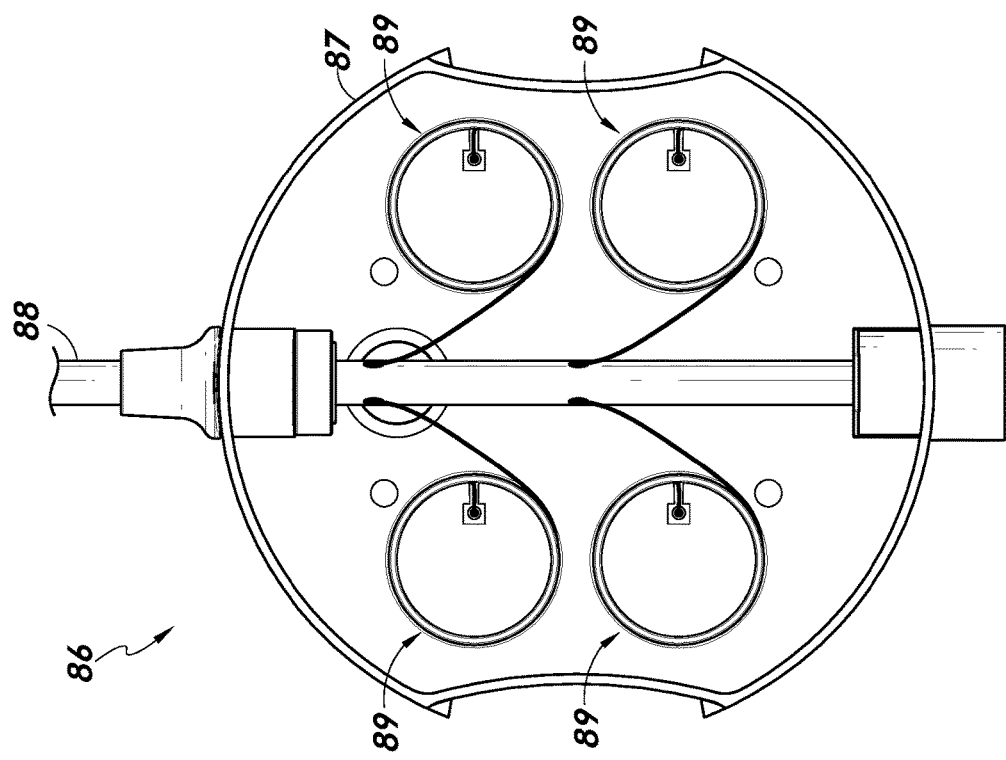
Figures 1, 7:
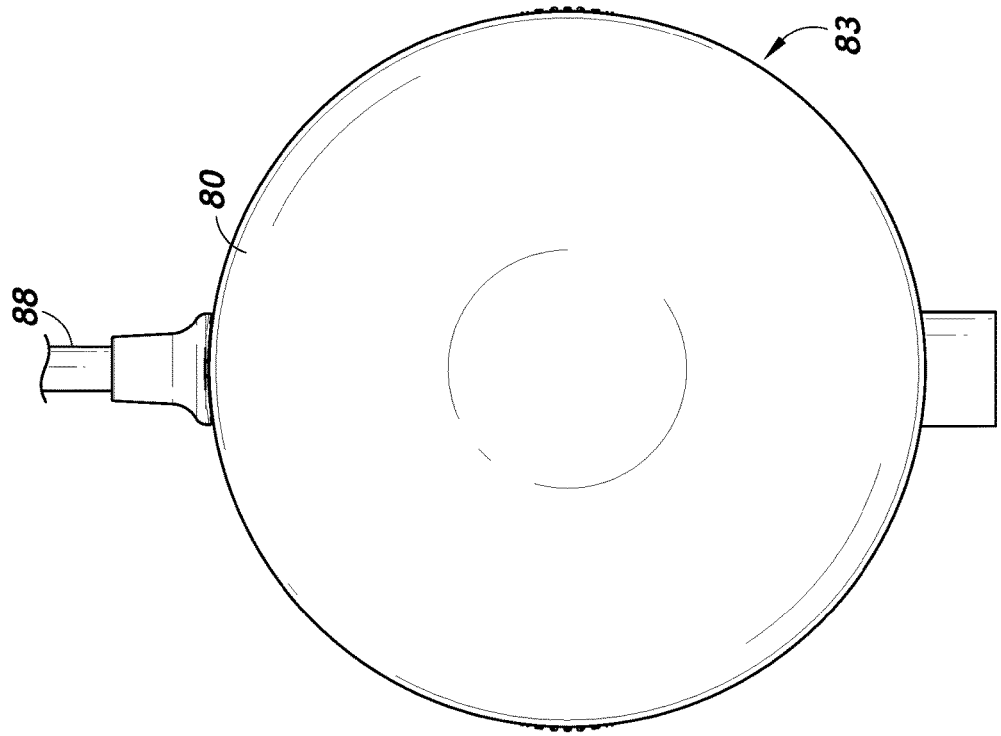

As shown in FIGS. 7-1 and 7-2, the robotically-controllable catheter 88 can also include a drive input assembly 89 configured to couple to a drive output assembly of a robotic arm and/or another device/interface. FIG. 7-1 illustrates the instrument base 87 with the top portion 80, while FIG. 7-2 illustrates the instrument base 87 with the top portion 80 removed to show the drive input assemblies 89 and other features. A drive output assembly can interface with the drive input assembly 89 to control articulation of the shaft 88 of the catheter. For example, the drive input assembly 89 can be coupled to one or more elongate movement members (illustrated in FIG. 7-2). The one or more elongate movement members can be slidably disposed within a portion of the shaft 88 and attach to the distal end portion of the shaft 88. The one or more elongate movement members can exit the shaft 88 in the instrument base 87 (e.g., towards the proximal end portion) and couple to the drive input assembly 89 within the instrument base 87. The one or more elongate movement members can exit the shaft 88 via one or more holes in the outer wall of the shaft 88. The drive output assembly can actuate (e.g., rotate) the drive input assembly 89 to pull (and/or release tension of) the one or more elongate movement members, resulting in actuation of the distal end portion of the shaft 88. Although various examples illustrate a spline interface coupling where a series of teeth on the outer and inner diameters of the outputs and inputs mate, the drive output assembly and the drive input assembly 89 can be coupled via any of a variety of teeth, protrusions, or other mating engagement features and arrangements.

In this example, the drive input assembly 89 includes one or more pulleys/spools configured to couple to the one or more elongate movement members. An elongate movement member (which can be implemented as a wire, for example) exits the shaft 88 within the instrument base 87 and winds around a spool to attach to the spool and/or to remove slack in the pull wire. The pull wire can exit the shaft 88 at the appropriate location to avoid contact with other internal components of the instrument base 87. For example, the shaft 88 can include the one or more holes in the outer wall of the shaft 88 at a particular distance from the proximal end of the shaft 88, such that the one or more pull wires can exit from one or more wire lumens in the outer wall of the shaft 88 and attach to the one or more pulleys without interfering with other components of the instrument base 88. The one or more pull wires can exit the shaft 88 at the same or different distances relative to the proximal end of the shaft 88.

At a top end of the spool, the pull wire can wrap into a channel/groove and can be secured/anchored at a distal end of the pull wire to a cavity using a stopper/enlargement/end feature. However, other types of attachment mechanisms can be used, such as any type of fastener, adhesive, sandwiching/pinching the wire, soldering a metal ball at an end to create an anchor, laser melting an end into a ball shape that can be used as an anchor, etc. For example, a ring can be placed over the top end to maintain/secure the pull wire. The pull wire can be coupled to the spool due to friction of the pull wire to the spool, tension of the pull wire, the stopper, and/or the ring. At a bottom end of the spool, the spool can include a coupling mechanism/coupler configured to interface with a drive output assembly. For example, the coupling mechanism can include a gear or other mechanism. Although various example features are shown for the drive input assembly 89, the drive input assembly 89 can be implemented in a variety of other manners.

To control articulation of the shaft 88, the one or more spools can be rotated to pull (or release tension of) the one or more pull wires attached thereto. For example, rotating the spool in a counterclockwise direction can cause the pull wire to more fully wraparound the spool, resulting in a pull motion of the pull wire. As such, the spool can be rotated to control an amount of slack/tension in the pull wire. In some examples, multiple spools are rotated at the same time (e.g., in a cooperative manner) to facilitate articulation of the shaft 88 in a particular direction. The spools can be rotated in the same or different directions to facilitate a particular movement. As noted above, a drive output assembly, such as that illustrated in FIG. 6, can control rotation of the one or more spools. In some embodiments, the catheter is configured to move in two directions, such as up and down or left, and right, based on manipulation of the one or more elongate movement members. In other embodiments, the catheter is configured to move in four directions, such as up, down, left, and right, based on manipulation of the one or more elongate movement members. In any event, the catheter can also be configured to be inserted/retracted, such as along a virtual rail, based on movement of the instrument base 87 (e.g., movement of a robotic arm attached to the instrument base 87).

Referring to FIG. 6, a medical instrument can be paired to an instrument driver 75. Like other instruments designed for use with a robotic system, a medical instrument can comprise an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs that extend through a drive interface 8 on instrument driver 75 at the distal end of robotic arm 76. When physically connected, latched, and/or coupled, the mated drive inputs 73 of instrument base 72 may share axes of rotation with the drive outputs in the instrument driver 75 to allow the transfer of torque from drive outputs to drive inputs 73. In some embodiments, the drive outputs may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope 52) or rigid (e.g., having properties similar to a laparoscope) or contain a customized combination of both flexible and rigid portions. When designed for laparoscopy, the distal end of a rigid elongated shaft may be connected to an end effector comprising a jointed wrist formed from a clevis with an axis of rotation and a surgical tool, such as, for example, a grasper or scissors, that may be actuated based on force from the tendons as the drive inputs rotate in response to torque received from the drive outputs of the instrument driver 75. When designed for endoscopy, the distal end of a flexible elongated shaft may include a steerable or controllable bending section that may be articulated and bent based on torque received from the drive outputs of the instrument driver 75.

Torque from the instrument driver 75 is transmitted down the elongated shaft 71 using tendons within the shaft 71. These individual tendons, such as pull wires, may be individually anchored to individual drive inputs 73 within the instrument handle 72. From the handle 72, the tendons are directed down one or more pull lumens within the elongated shaft 71 and anchored at the distal portion of the elongated shaft 71. In laparoscopy, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools, irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In an example, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongate shaft 71. The resulting entanglement of such tendons may disrupt any control methods intended to predict movement of the flexible elongate shaft during an endoscopic procedure.

In an alternative design for an instrument driver and instrument, the axes of the drive units are parallel to the axis of the elongated shaft of the instrument. A circular instrument driver can comprise four drive units with their drive outputs aligned in parallel at the end of a robotic arm. The drive units, and their respective drive outputs, are housed in a rotational assembly of the instrument driver that is driven by one of the drive units within the assembly. In response to torque provided by the rotational drive unit, the rotational assembly rotates along a circular bearing that connects the rotational assembly to the non-rotational portion of the instrument driver. Power and controls signals may be communicated from the non-rotational portion of the instrument driver to the rotational assembly through electrical contacts that may be maintained through rotation by a brushed slip ring connection (not shown). In other embodiments, the rotational assembly may be responsive to a separate drive unit that is integrated into the non-rotatable portion, and thus not in parallel to the other drive units. The rotational mechanism allows the instrument driver to rotate the drive units, and their respective drive outputs, as a single unit around an instrument driver axis.

Like earlier disclosed embodiments, an instrument may comprise of an elongated shaft portion 88 and an instrument base 87 comprising a plurality of drive inputs 89 (such as receptacles, pulleys, and spools) that are configured to receive the drive outputs in the instrument driver. Unlike prior disclosed embodiments, instrument shaft 88 extends from the center of instrument base 87 with an axis substantially parallel to the axes of the drive inputs 89, rather than orthogonal as in the design of FIG. 7-2.

When coupled to the rotational assembly of the instrument driver, the medical instrument 86, comprising instrument base 87 and instrument shaft 88, rotates in combination with the rotational assembly about the instrument driver axis. Since the instrument shaft 88 is positioned at the center of instrument base 87, the instrument shaft 88 is coaxial with instrument driver axis 85 when attached. Thus, rotation of the rotational assembly causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs, drive inputs 89, and instrument shaft 88 allows for the shaft rotation without tangling any control tendons.

E. Navigation and Control

Traditional endoscopy may involve the use of fluoroscopy (e.g., as may be delivered through a C-arm as shown at FIG. 5) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, real-time video imaging, computer vision, real-time EM tracking, and robot command data may be used individually or in combination to achieve a radiation-free operating environment. In other cases, where radiation-based imaging modalities are still used, the pre-operative mapping, real-time video imaging, computer vision, real-time EM tracking, and robot command data may be used individually or in combination to improve upon the information obtained solely through radiation-based imaging modalities.

FIG. 8 is a block diagram illustrating a localization system 90 that estimates a location of one or more elements of the robotic system, such as the location of the medical instrument (such as an endoscope 52, for example), in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 and cart 11 shown in FIG. 1, the bed shown in FIG. 5, etc.

As shown at FIG. 8, the localization system 90 may include a localization module 95 that processes input data 91-94 to generate location data 96 for the distal tip of a medical instrument. The location data 96 may be data or logic that represents a location and/or orientation of the distal end of the medical instrument relative to a frame of reference. The frame of reference can be a frame of reference relative to the anatomy of the patient or to a known object, such as pre-operative CT images, an EM field generator, or the like (see discussion below for the EM field generator).

The various input data 91-94 are now described in greater detail. Pre-operative mapping may be accomplished through the use of the collection of low dose CT scans. Pre-operative CT scans generate two-dimensional images, each representing a "slice" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as preoperative model data 91. The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide video or vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope 52 or an instrument advance through a working channel of the endoscope 52). For example, using the preoperative model data 91, the robotic system may generate a library of expected endoscopic images from the model based on the expected path of travel of the endoscope 52, each image linked to a location within the model. Intra-operatively, this library may be referenced by the robotic system 10 in order to compare real-time images captured at the camera (e.g., a camera at a distal end of the endoscope 52) to those in the image library to assist localization.

Other computer vision-based tracking techniques use feature tracking to determine motion of the camera, and thus the endoscope 52. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based methods or techniques.

Optical flow, another computer vision-based technique, may analyze the displacement and translation of image pixels in a video sequence in the vision data 92 to infer camera movement. Through the comparison of multiple frames over multiple iterations, movement and location of the camera (and thus the endoscope 52) may be determined.

The localization module 95 may use real-time EM tracking to generate a real-time location of the endoscope 52 in a global coordinate system that may be registered to the patient's anatomy, represented by the preoperative model data 91. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope 52) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 8 shows, a number of other input data can be used by the localization module 95. For example, although not shown in FIG. 15, an instrument utilizing shape-sensing fiber can provide shape data that the localization module 95 can use to determine the location and shape of the instrument. Additionally or alternatively, an ultrasound imaging system may be provided, or one or more gyroscopes and/or accelerometers may be disposed at or in the instrument and provide inertial measurement data, either of which may also be used by the localization module 95 in combination with EM, vision, topological modeling, and/or any other data source to estimate the position of the medical instrument within the network.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems 10 discussed herein may be designed to incorporate a combination of one or more of the technologies above. The robotic system's computer-based control system 50, based in the tower 30, bed and/or cart 11, may store computer program instructions, for example, within a non-transitory computer-readable storage medium such as a persistent magnetic storage drive, solid state drive, or the like, that, upon execution, cause the control system 50 to receive and analyze sensor data and user commands, generate control signals throughout the robotic system 10, and display the navigational and localization data, such as the position of the instrument within the global coordinate system, anatomical map, etc.

The control system 50 can be configured to provide various functionality to assist in performing a medical procedure. In some embodiments, the control system 50 can be coupled to the robotic system 10 and operate in cooperation with the robotic system 10 to perform a medical procedure on the patient. For example, the control system 50 can communicate with the robotic system 10 via a wireless or wired connection (e.g., to control the robotic system 10 and/or the scope 52, receive images captured by the scope 52, etc.), provide fluids to the robotic system 10 via one or more fluid channels, provide power to the robotic system 10 via one or more electrical connections, provide optics to the robotic system 10 via one or more optical fibers or other components, and so on. Further, in some embodiments, the control system 50 can communicate with a needle and/or endoscope 52 to receive position data 94 therefrom. Moreover, in some embodiments, the control system 50 can communicate with the table to position the table in a particular orientation or otherwise control the table. Further, in some embodiments, the control system 50 can communicate with the EM field generator (not shown) to control generation of an EM field in an area around the patient.

The control system 50 can include various I/O devices configured to assist the physician or others in performing a medical procedure. For example, the control system 50 can include certain input/output (I/O) components configured to allow for user input to control the scope 52, such as to navigate the scope 52 within the patient. In some embodiments, for example, the physician can provide input to the control system 50 and/or robotic system 10, wherein in response, control signals can be sent to the robotic system 10 to manipulate the scope 52. To facilitate the functionality of the control system 50, the control system can include various components (sometimes referred to as "subsystems"). For example, the control system 50 can include control electronics/circuitry 60, as well as one or more power sources, pneumatic devices, optical sources, actuators, data storage devices, and/or communication interfaces. In some embodiments, the control system 50 includes control circuitry 60 comprising a computer-based control system that is configured to store executable instructions, that when executed, cause various operations to be implemented. In some embodiments, the control system 50 is movable, while in other embodiments, the control system 50 is a substantially stationary system. Although various functionality and components are discussed as being implemented by the control system 50, any of such functionality and/or components can be integrated into and/or performed by other systems and/or devices, such as the robotic system 10, for example.

The various components of the robotic system 10 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Furthermore, in some embodiments, the various components of the robotic system 10 can be connected for data communication, fluid/gas exchange, power exchange, and so on via one or more support cables, tubes, or the like.

The robotic system 10 may include certain control circuitry 60 configured to perform certain of the functionality described herein. The control circuitry 60 may be part of the robotic system 10, the control system 50, or both. That is, references herein to control circuitry 60 may refer to circuitry embodied in a robotic system 10, a control system 50, or any other component of a medical system, such as the robotic medical system 10 shown in FIG. 1. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry 60 referenced herein may further include one or more circuit substrates (e.g., printed circuit boards), conductive traces and vias, and/or mounting pads, connectors, and/or components. Control circuitry 60 referenced herein may further comprise one or more storage devices, which may be embodied in a single memory device, a plurality of memory devices, and/or embedded circuitry of a device.

Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry 60 comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

The control circuitry 60 may comprise a computer-readable medium storing hard-coded and/or operational instructions corresponding to at least some of the steps and/or functions illustrated in one or more of the present figures and/or described herein. Such computer-readable medium can be included in an article of manufacture in some instances. The control circuitry 60 may be entirely locally maintained/disposed or may be remotely located at least in part (e.g., communicatively coupled indirectly via a local area network and/or a wide area network).

In some embodiments, at least a portion of the control circuitry 60 is integrated with the robotic system 10 or another system communicatively coupled to the robotic system 10. In some embodiments, at least a portion of the control circuitry 60 is integrated with the control system 50. Therefore, any description of functional control circuitry herein may be understood to be embodied in either the robotic system 10, the control system 50, or both, and/or at least in part in one or more other local or remote systems/devices.

The control circuitry 60 may use a three-dimensional (3D) map of a patient and/or pre-determined computer models of a t least a portion of the patient to control a medical instrument (e.g., endoscope 52). For example, the control circuitry 60 can be configured to provide control signals to the robotic arms 12, 76 of the robotic system 10 to manipulate the relevant instrument to position the same at a target location, position, and/or orientation/alignment.

In some embodiments, a user can manually manipulate a robotic arm 12, 76 of the robotic system 10 without using the user controls. For example, during setup in a surgical operating room, a user may move the robotic arms 12, 76 and/or any other medical instruments to provide desired access to a patient. The robotic system 10 may rely on force feedback and inertia control from the user to determine appropriate configuration of the robotic arms 12, 76 and associated instrumentation.

Display device(s) of the control system 50 may be integrated with the user controls, for example, as a tablet device with a touchscreen providing for user input. The display device(s) can be configured to provide data and input commands to the robotic system 10 using integrated display touch controls. The display device(s) can be configured to display graphical user interfaces showing information about the position and orientation of various instruments operating within the patient and/or system based on information provided by one or more position sensors. In some embodiments, position sensors associated with medical instruments (e.g., an endoscope 52) may be configured to generate signals indicative of position and transmit the same on wires and/or transmitters coupled to the sensors. Such connectivity components may be configured to transmit the position information to the console base for processing thereof by the control circuitry 60 and for presentation via the display device(s).

2. Navigation of Luminal Networks

The various robotic systems discussed above can be employed to perform a variety of medical procedures, such as endoscopic and laparoscopic procedures. During certain procedures, a medical instrument, such as a robotically-controlled medical instrument, is inserted into a patient's body. Within the patient's body, the instrument may be positioned within a luminal network of the patient. As used herein, the term luminal network refers to any cavity structure within the body, whether comprising a plurality of lumens or branches (e.g., a plurality of branched lumens, as in the lung or blood vessels) or a single lumen or branch (e.g., within the gastrointestinal tract). During the procedure, the instrument may be moved (e.g., navigated, guided, driven, etc.) through the luminal network to one or more areas of interest. Movement of the instrument through the system may be aided by the navigation or localization system 90 discussed above, which can provide positional information about the instrument to a physician controlling the robotic system.

Figure 9:
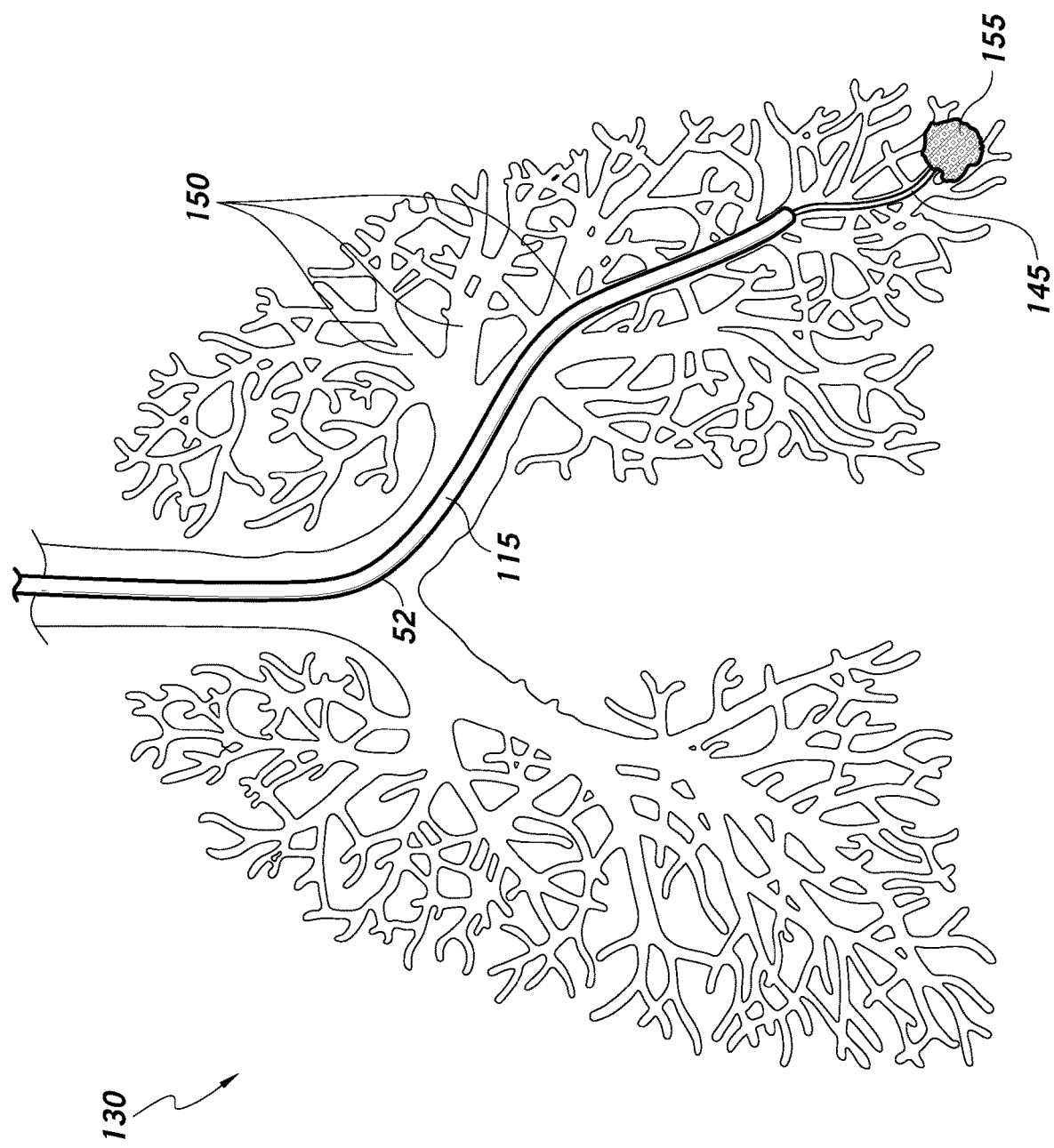
FIG. 9 illustrates an example of an instrument navigating a luminal network.

FIG. 9 illustrates an example luminal network 130 of a patient. In the illustrated embodiment, the luminal network 130 is a bronchial network of airways 150 (i.e., lumens, branches) of the patient's lung. Although the illustrated luminal network 130 is a bronchial network of airways 150 within the patient's lung, this disclosure is not limited to only the illustrated example. The robotic systems and methods described herein may be used to navigate any type of luminal network, such as bronchial networks, renal networks, cardiovascular networks (e.g., arteries and veins), gastrointestinal tracts, urinary tracts, etc.

As illustrated, the luminal network 130 comprises a plurality of lumens 150 that are arranged in a branched structure. In general, the luminal network 130 comprises a three-dimensional structure. For ease of illustration, FIG. 9 represents the luminal network 130 as a two-dimensional structure. This should not be construed to limit the present disclosure to two-dimensional luminal networks in any way.

FIG. 9 also illustrates an example of a medical instrument positioned within the luminal network 130. The medical instrument is navigated through the luminal network 130 towards an area of interest (e.g., nodule 155) for diagnosis and/or treatment. In the illustrated example, the nodule 155 is located at the periphery of the airways 150, although the area(s) of interest can be positioned anywhere within the luminal network 130 depending on the patient and procedure.

In the illustrated example, the medical instrument comprises an endoscope 52. The endoscope 52 can include a sheath 115 and a leader 145. In some embodiments, the sheath 115 and the leader 145 may be arranged in a telescopic manner. For example, the leader 145 may be slideably positioned inside a working channel of the sheath 115. The sheath 115 may have a first diameter, and its distal end may not be able to be positioned through the smaller-diameter airways 150 around the nodule 155. Accordingly, the leader 145 may be configured to extend from the working channel of the sheath 115 the remaining distance to the nodule 155. The leader 145 may have a lumen through which instruments, for example biopsy needles, cytology brushes, and/or tissue sampling forceps, can be passed to the target tissue site of the nodule 155. In such implementations, both the distal end of the sheath 115 and the distal end of the leader 145 can be provided with optical sensors or camera (e.g., imaging device 315 in FIG. 10), EM instrument sensors (e.g., EM instrument sensors 305 in FIG. 10), and/or other sensors for tracking their position within the airways 150. This telescopic arrangement of the sheath 115 and the leader 145 may allow for a thinner design of the endoscope 52 and may improve a bend radius of the endoscope 52 while providing a structural support via the sheath 115.

In other embodiments, the overall diameter of the endoscope 52 may be small enough to reach the periphery without the telescopic arrangement, or may be small enough to get close to the periphery (e.g., within 2.5-3 cm) to deploy medical instruments through a non-steerable catheter. The medical instruments deployed through the endoscope 52 may be equipped with optical sensors or camera (e.g., imaging device 315 in FIG. 10), EM instrument sensors (e.g., EM instrument sensors 305 in FIG. 10), and the image-based branch detection and mapping navigation techniques described below can be applied to such medical instruments.

As shown, to reach the nodule 155, the instrument (e.g., endoscope 52) must be navigated or guided through the lumens or branches 150 of the luminal network. An operator (such as a physician) can control the robotic system to navigate the instrument to the nodule 155. The operator may provide inputs for controlling the robotic system 10.

Figure 10:
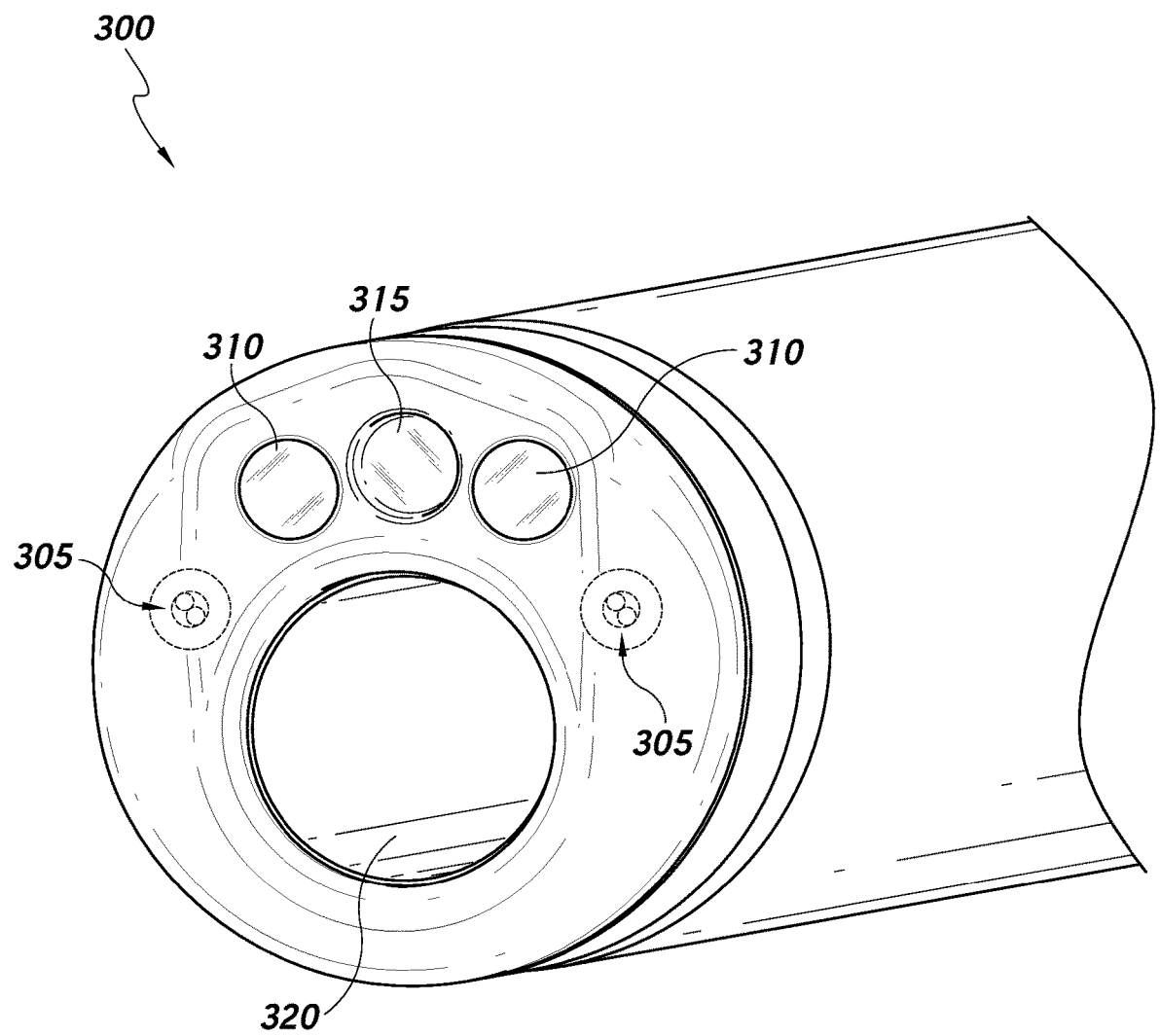
FIG. 10 illustrates a distal end of an embodiment of a medical instrument.

FIG. 10 illustrates a detail view of a distal end of an example medical instrument 300. The medical instrument 300 of FIG. 10 may be representative of the endoscope 52 or steerable catheter 145 of FIG. 9. The medical instrument 300 may be representative of any medical instrument described throughout the disclosure, such as the endoscope 52 of FIG. 1, the ureteroscope 32 of FIG. 3, a laparoscope, etc. In FIG. 10, the distal end of the instrument 300 includes an imaging device 315, illumination sources 310, and ends of EM sensor coils 305, which form an EM instrument sensor. The distal end further includes an opening to a working channel 320 of the instrument 300 through which surgical instruments, such as biopsy needles, cytology brushes, forceps, etc., may be inserted along the instrument shaft, allowing access to the area near the instrument tip.

Imaging device 315, EM coils 305, and/or other components located on the distal end of the instrument 300 may be used with a location tracking system to detect the position and orientation of the distal end of the instrument 300 while it is positioned within a luminal network 130. In some embodiments, the coils 305 may be angled to provide sensitivity to EM fields along different axes, giving the disclosed navigational systems the ability to measure a full 6 degrees of freedom (DoF): three positional DoF and three angular DoF. In other embodiments, only a single coil 305 may be disposed on or within the distal end with its axis oriented along the instrument shaft. Due to the rotational symmetry of such a system, it may be insensitive to roll about its axis, so only five degrees of freedom may be detected in such an implementation. Alternatively or additionally, other types of position sensors may be employed.

The illumination sources 310 provide light to illuminate a portion of an anatomical space. For example, the light provided by the illumination sources 310 can be used in combination with the imaging device 315 or other camera or video capturing device. The illumination sources can each be one or more light-emitting devices configured to emit light at a selected wavelength or range of wavelengths. The wavelengths can be any suitable wavelength, for example, visible spectrum light, infrared light, x-ray (e.g., for fluoroscopy), to name a few examples. In some embodiments, illumination sources 310 can include light-emitting diodes (LEDs) located at the distal end of the instrument 300. In some embodiments, illumination sources 310 can include one or more fiber optic fibers extending through a length of the endoscope 52 to transmit light through the distal end from a remote light source, for example, an x-ray generator. Where the distal end includes multiple illumination sources 310 these can each be configured to emit the same or different wavelengths of light as one another.

The imaging device 315 can include any photosensitive substrate or structure configured to convert energy representing received light into electric signals, for example, a charge-coupled device (CCD) or complementary metal-oxide semiconductor (CMOS) image sensor. Some examples of imaging device 315 can include one or more optical fibers, for example, a fiber optic bundle, configured to transmit light representing an image from the distal end of the endoscope 52 to an eyepiece and/or image sensor near the proximal end of the endoscope 52. Imaging device 315 can additionally include one or more lenses and/or wavelength pass or cutoff filters as required for various optical designs. The light emitted from the illumination sources 310 allows the imaging device 315 to capture still or video image data 92 of the interior of a patient's luminal network. These images can then be transmitted as individual frames or series of successive frames (e.g., a video) to a computer system such as the control system 50. As mentioned above and as will be described in greater detail below, the images captured by the imaging device 315 (e.g., video data 92 of FIG. 8) can be utilized by the navigation or localization system 90 to determine or estimate the position of the instrument 300 (e.g., the position of the distal tip of the instrument 300) within a luminal network 130.

3. Image-Based Localization

Embodiments of the disclosure relate to systems and techniques for image-based localization. As used herein, image-based localization, which also includes vision-based camera pose estimation, may refer to modeling internal anatomical features of one or more branches 150 of a luminal network 130. For example, an image-based localization system 90 may generate models of the internal anatomical structure of the luminal network 130 based at least in part on image data 92 captured of the interior of the luminal network 130 using imaging devices 315 positioned on an instrument 300 within the luminal network 130. The image-based localization system 90 may analyze the models to estimate a location of the instrument 300 within the luminal network 130. For example, an image-based localization system 90 may be configured to identify which of a plurality of second models generated using data from a second imaging technique (e.g., CT scan data 91) has a highest similarity to a first model generated using data from a first imaging technique (e.g., video data 92, in the case of vision-based camera pose estimation). These systems and techniques may be used to determine or estimate the position and orientation of the instrument 300 within the luminal network 130 based at least in part on the identified second model. In certain implementations, these systems and techniques may be used in conjunction with various other navigation and localization modalities (e.g., as described above with reference to FIG. 8).

A. Overview of Image-Based Localization

The ability to navigate inside a luminal network 130 may be a feature of the robotically-controlled surgical systems 10 described herein. As used herein, localization may refer to locating or determining the position of an instrument 300 within an internal anatomical structure, such as a luminal network 130. The determined position may be used to help guide the instrument 300 to one or more particular areas of interest within the luminal network 130. In some embodiments, the robotically-controlled surgical systems 10 utilize one or more independent sensing modalities to provide intra-operative navigation for the instrument 300. As shown in FIG. 8, the independent sensing modalities may provide independent data (e.g., CT image data 91, vision data 92, EM data 93, robotic command and kinematics data 94, and so forth). These independent sensing modalities may source data to the localization module 95, which is configured to provide estimates of position and orientation. The estimates can be used to generate a navigation output 96, for example, which can be used by the system 10 or displayed to the user. In an example, image-based localization based on vision data 92, which can include referencing pre-operative CT image data 91, can provide an estimate of the position within a lumen or branch 150 of a luminal network 130 of an imaging device 315 of the instrument 300, based at least in part on an image or images captured by the imaging device 315. In some embodiments, the estimate provided by image-based localization may be used alone or with other position estimates to determine a final position estimate that can be used by the system 10 or displayed to the user.

In some embodiments, there can be multiple sources of imaging data that provide vision data 92 to the localization module 95, to output a position estimate (based at least on part on the vision data 92). This disclosure refers to an image-based localization module 95 that generates internal anatomical models based on vision data 92 (e.g., based on data from multiple images) and estimates the current position of the instrument 300 by mapping the models to a specific location within the anatomical branches 150 of the luminal network 130. As will be described in greater detail below, in some embodiments, the localization module 95 may use a current or previous position estimate determined by navigation or by the localization system 90 (that can be based on one or a plurality of sensing modalities) to initialize the system 90 for a subsequent estimate. Stated another way, the image-based localization systems and methods described herein may be configured to provide a position estimate to the navigation or localization module 95 of where the instrument 300 is positioned in the luminal network 130. In some embodiments, the image-based localization systems and methods described herein may be independent of any other modality. In some embodiments, the image-based localization systems and methods described herein may base estimates on prior position estimates determined using a plurality sensing modalities.

B. Image-Based Data Capture

Figure 11:
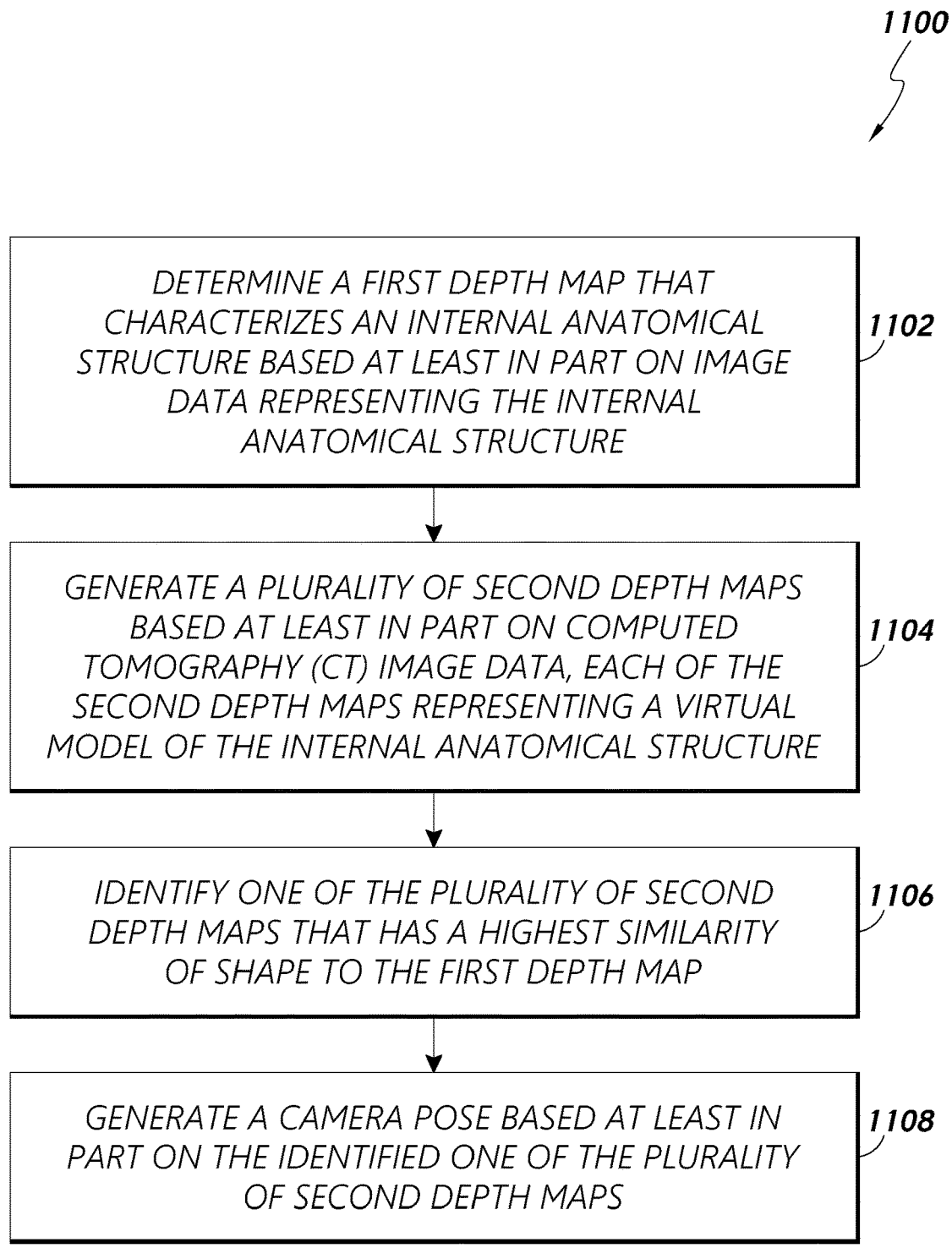
FIG. 11 depicts a flowchart illustrating an example method for image-based localization.

FIG. 11 illustrates an example method 400 of generating a camera pose representative of a spatial location within an internal anatomical structure, such as within a luminal network 130. The camera pose can be defined in coordinates relative to pre-operative CT image data 91. In other words, an example method 400 for image-based localization is illustrated. The method 400 may be implemented in various robotically-controlled surgical systems 10 as described herein. The method 400 may include multiple steps or blocks, as described herein with reference to FIG. 12.

At block 402, the method 400 includes determining a first depth map 435 that characterizes an internal anatomical structure based at least in part on image data representing the internal anatomical structure. As noted above, during a medical procedure, an instrument may be positioned within a luminal network 130 (see FIG. 9). As shown at FIG. 10, the instrument may include an imaging device 315 (such as a camera) positioned thereon. The imaging device 315 may capture images of the interior of the luminal network 130. For example, at a particular instant, the imaging device 315 may capture an image of the interior of the particular branch 150 of the luminal network 130 in which the instrument is currently positioned. The captured image results in captured image data 92 representing the internal anatomical structure of the luminal network 130. In various embodiments, the imaging device 315 comprises a video camera and the captured image data 92 comprises video data. The captured image data 92 is processed by the localization module 95 as described above, and as will be described further below. For instance, the first depth map 435 is generated by the localization module 95 using the captured image data 92. In some cases, a convolutional neural network (CNN) may be used to generate the first depth map 435 by the localization module 95.

At block 404, the method 400 includes generating a plurality of second depth maps 455 based at least in part on image data, such as computed tomography (CT) image data 91, where each of the second depth maps 455 is representing a virtual model of the internal anatomical structure. As described above, multiple pre-operative CT images 91 of the luminal network 130 may be collected to form a virtual model of the internal anatomical structure of the luminal network 130. The pre-operative CT images 91 are processed by the localization module 95 as described above, and as will be described further below. For instance, the plurality of second depth maps 455 are generated by the localization module 95 using the pre-operative CT image data 92. In some embodiments, the generation of second depth maps 455 is an iterative process. For instance, the iterative process can include using one of the plurality of second depth maps of a previous iteration to initialize generating the plurality of second depth maps 455 for the current iteration.

At block 406, the method 400 includes identifying one of the plurality of second depth maps 455 that has a highest similarity of shape to the first depth map 435. As described further below, each of the plurality of second depth maps 455 are analyzed against the first depth map 435 for similarity of shape. The second depth map 455 that has a highest similarity of shape to the first depth map 435 is identified as a "candidate depth map" 465 for generating the output, a camera pose estimation 475.

At block 408, the method 400 includes generating a camera pose 475 based at least in part on the identified one of the plurality of second depth maps 455. In other words, the estimated camera pose 475 is determined at least in part on the candidate depth map 465, and may be output to the user or processed to generate real-time navigation/localization output data 96, which may be further processed to generate control signals for the robotic arms 12, 76 or other components of the robotic system 10, output to the operator in visual form on a display, or otherwise used to guide the robotic system 10, another peripheral system, or the operator. The estimated camera pose 475 can be defined in coordinates relative to the pre-operative CT image data 91 for convenience. A virtual camera pose 475 can be generated for each of the second depth maps 455 of the plurality of second depth maps in some implementations.

In some embodiments, as discussed further below, camera pose 475 parameters are estimated by solving a transformation matrix between a 3D point cloud of the virtual model of the internal anatomical structure and a point cloud inverse projected from the first depth map 435. A convolutional neural network (CNN) can be employed to solve the transformation matrix and estimate the camera pose 475 parameters. A desired location in one of the plurality of second depth maps 455 that corresponds to a location in one or more video images 92, can be identified for registration with the first depth map 435.

C. Image-Based Data Analysis

Figure 12:
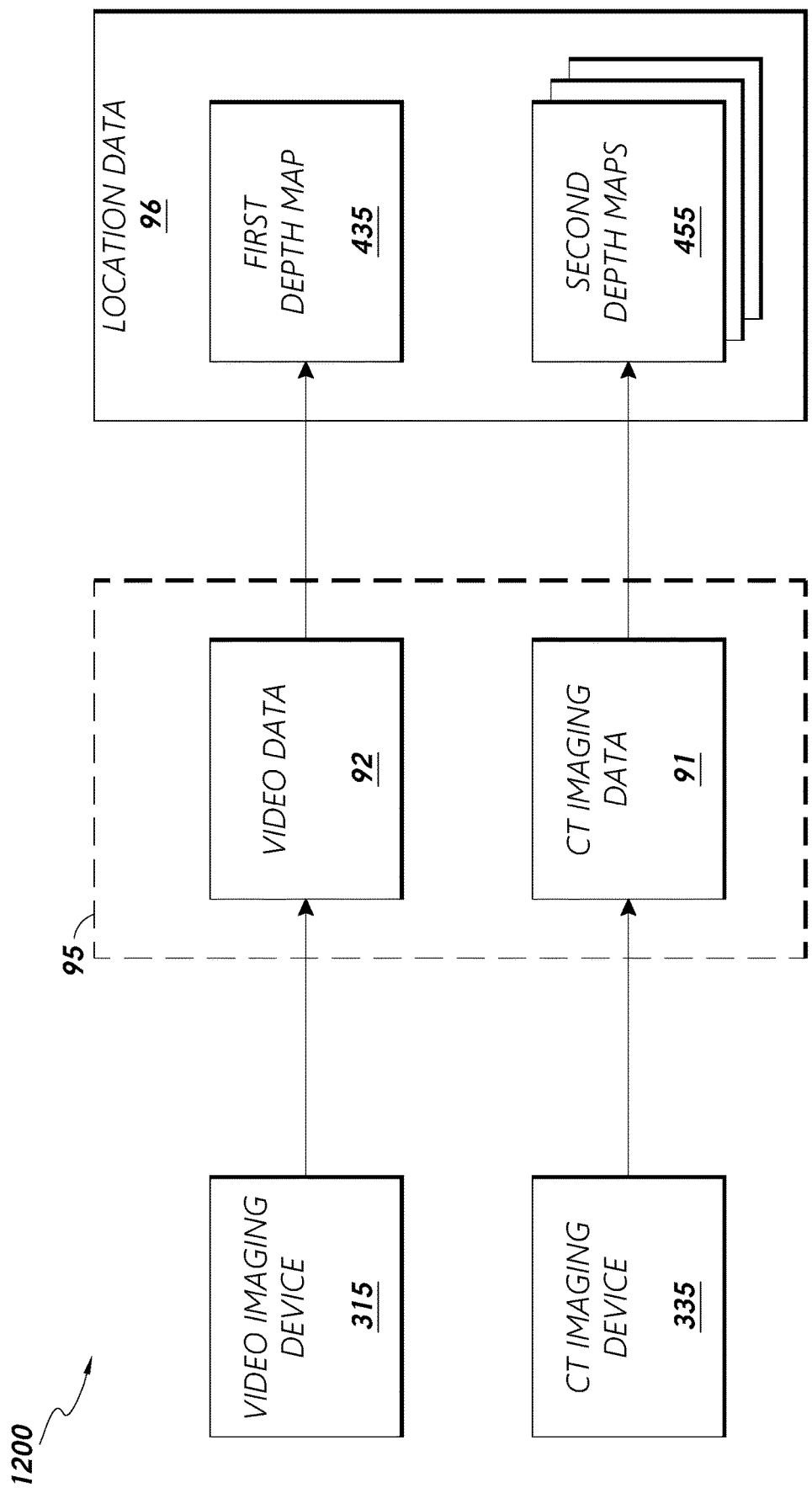
FIG. 12 illustrates a block diagram of a portion of an example localization module for image processing.

FIG. 12 shows an example high-level overview block diagram of some data processes of the localization module 95. Referring to FIG. 12, the localization module 95 generates separate models of the internal anatomical structure of the luminal network 130 using different data from separate sources. For instance, at least one first model 435 of the luminal network 130 (or a branch 150 of the luminal network 130 of interest) is generated based on image data 92 from the imaging device 315 disposed at the distal end of the instrument positioned within the luminal network 130. The image data 92 may be real-time image data reflecting the real-time location of the instrument within the luminal network 130. The model 435 formed from the image data 92 can also be a real-time model of the branch 150 of the luminal network 130 at the location of the instrument. This model 435 may be referred to as a "depth map" since it effectively comprises a 3D map of the portion of the luminal network 130 of interest, giving relative spatial information in the 3D sense (for instance with x, y, and z dimensions or coordinates) of the branch 150. The first depth map 435 is generated by the localization module 95 and comprises location data 96 that may be stored in data storage 415, for example.

Additionally, a plurality of second models 455 (second depth maps 455) of the luminal network 130 (or a portion of the luminal network 130 of interest) are generated based at least in part on image data 91 from the pre-operative CT images of a CT scanning device 335, as discussed previously. Multiple models 455 can be generated from multiple CT images of the luminal network 130 collected. Since the CT image data 91 is pre-operative, the CT image data 91 can provide reference for a coordinate system or other reference for navigation and localization. Further, the image data 92 collected from the imaging device 315 can be referenced to the CT image data 91, as discussed below. The second depth maps 455 are generated by the localization module 95 and comprise location data 96 that may also be stored in data storage 415, for example.

By modeling at least a portion of the luminal network 130 via the depth maps 435 and 455, the method 400 can provide virtual renderings or virtual models of the portion of the luminal network 130, by which an estimate of position for the instrument can be determined. For example, using the method 400, the system or the instrument can identify features that the instrument "sees" and use this information to estimate where the instrument is within the luminal network 130. In some embodiments, the instrument comprises an endoscope 52. In some embodiments, the luminal network 130 comprises a bronchial network of a lung, a gastrointestinal tract, or a renal network of a kidney, although navigation of other luminal networks is also possible.

Figure 13:
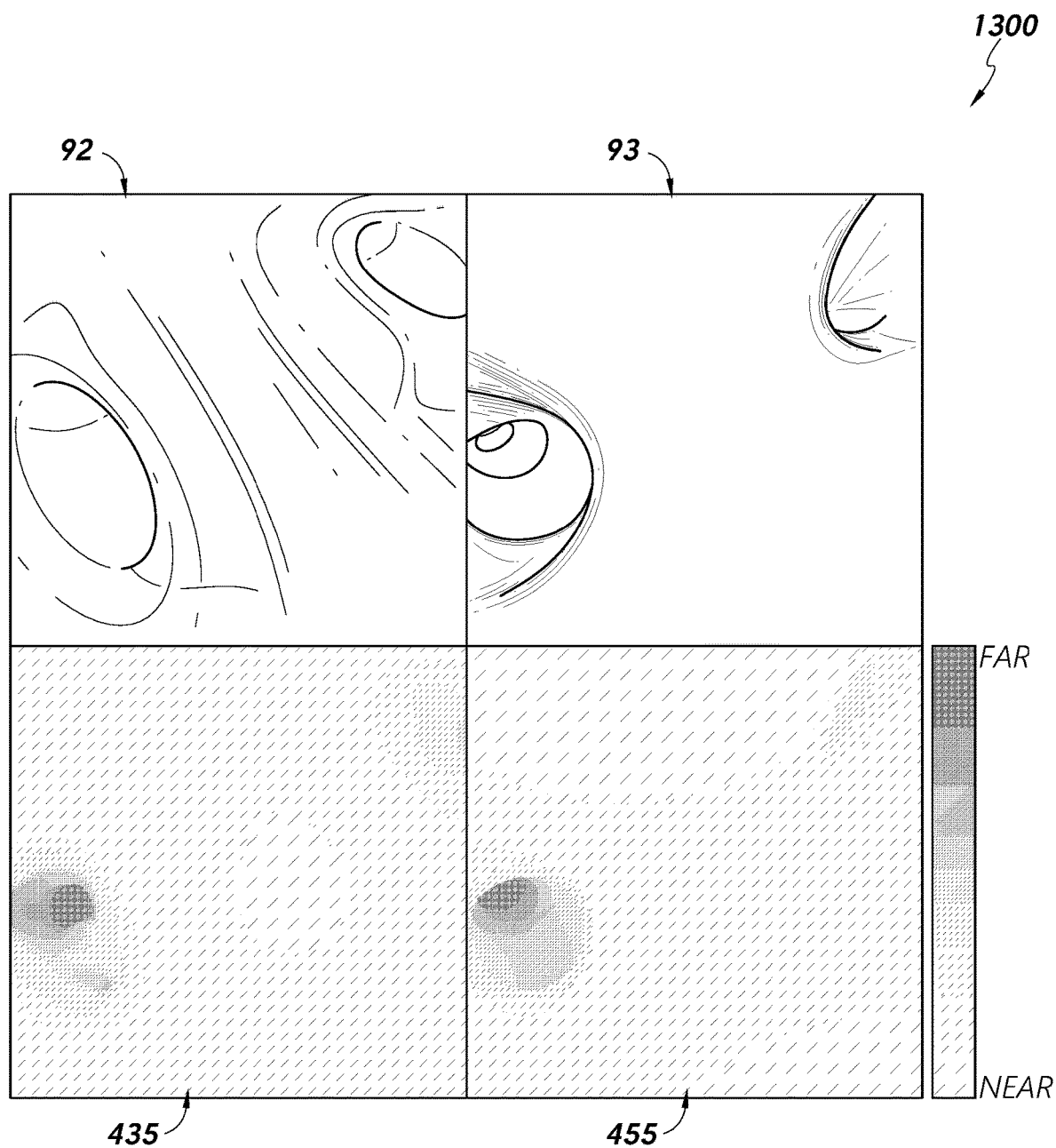
FIG. 13 illustrates examples of a video image and a CT image, each with associated depth maps.

Referring to FIG. 13, an example of image data 92 (e.g., video data 92) is shown as captured by an imaging device 315 such as a video camera within a luminal network 130 (e.g., airway). The video image data 92 shows an example portion of the luminal network 130 with branches 150 as well as contours, textures, features, moisture droplets, and so forth. A corresponding depth map 435 is extracted from the video image data 92. The advantage of using a depth map 435 instead of a video image 92 is that the depth map 435 provides better generalizability than a corresponding video image 92. For example, with reference to airways, the appearance of the endobronchial surface often varies from patient to patient. It is also likely to have some image artifacts including water bubbles in the video image 92.

Therefore, generating a patient-specific virtual rendering of the endoluminal surface with texture such as vessels, blood spots or bubbles can be challenging. Depth maps 435 preserve the airway structures and remove the unnecessary surface texture of the video images 92.

Also shown at FIG. 13 is an example of a virtual camera image 93 of the relatively same area of the luminal network 130 generated using pre-operative CT image data 91, as captured by a CT imaging device 335. The virtual camera images 93 are generated using a 3D CT airway model reconstructed from the original pre-operative CT scans 91, and may be captured in multiple locations and orientations around the relatively same area of the luminal network 130. The corresponding second depth map 455 of each of the multiple virtual camera images 93 can also be generated using a virtual rendering approach. A second depth map 455 corresponding to the example virtual camera image 93 is shown at FIG. 13. One or more of the second depth maps 455 may have a similar shape to the first depth map 435 generated from the video image data 92. The localization module 95 analyzes and compares each of the second depth maps 455 to the first depth map 435 to find a second depth map 455 with a greatest similarity to the first depth map 435.

The localization module 95 can perform conversion from a video image 92 to a depth map 435 with a convolutional neural network (CNN) that performs domain adaptation. For example, using machine learning, the localization module 95 can extract multi-dimensional information from digital images such as the video images 92. The multi-dimensional information can be formed into the depth maps 435, with a mapping function. The mapping function Z=G(I) can be learned with supervised learning if known paired video images and corresponding depth maps are available. A dataset comprised of previously paired images and depth maps can be used to train the mapping function from the source domain (video images 92) to the target domain (depth maps 435) based on a deep feature space. Alternatively, when perfectly paired data are difficult to obtain, the mapping function can also be achieved by unsupervised learning methods such as generative adversarial learning with a cyclic consistency that does not require paired data. The generated first depth maps 435 and second depth maps 455 can be stored as location data 96.

The localization module 95, and particularly the conversion process may be embodied in certain control circuitry 60, including one or more processors, data storage devices, connectivity features, substrates, passive and/or active hardware circuit devices, chips/dies, and/or the like. For example, the localization module 95 may be embodied in the control circuitry 60 shown in FIG. 1 and described above. The localization module 95 may employ machine learning functionality to perform automatic localization and navigation with respect to internal patient anatomy. The localization module 95 may be configured to operate on certain image-type data structures, such as image data 92 representing at least a portion of a luminal network 130 associated with one or more medical procedures. Such input data/data structures may be operated on in some manner by certain control circuitry 60 associated with an image processing portion of the localization module 95. The control circuitry 60 may comprise any suitable or desirable transform and/or classification architecture, such as any suitable or desirable artificial neural network architecture such as a convolutional neural network. For example, the localization module 95 may implement a deep learning architecture that takes in an input image, applies layers of filters with learnable weights/biases to transform the image into another domain or differentiate one from the other for classification. Filters/characteristics used may be hand-engineered or may be learned through machine learning.

D. Camera Pose Estimation

Figure 14:
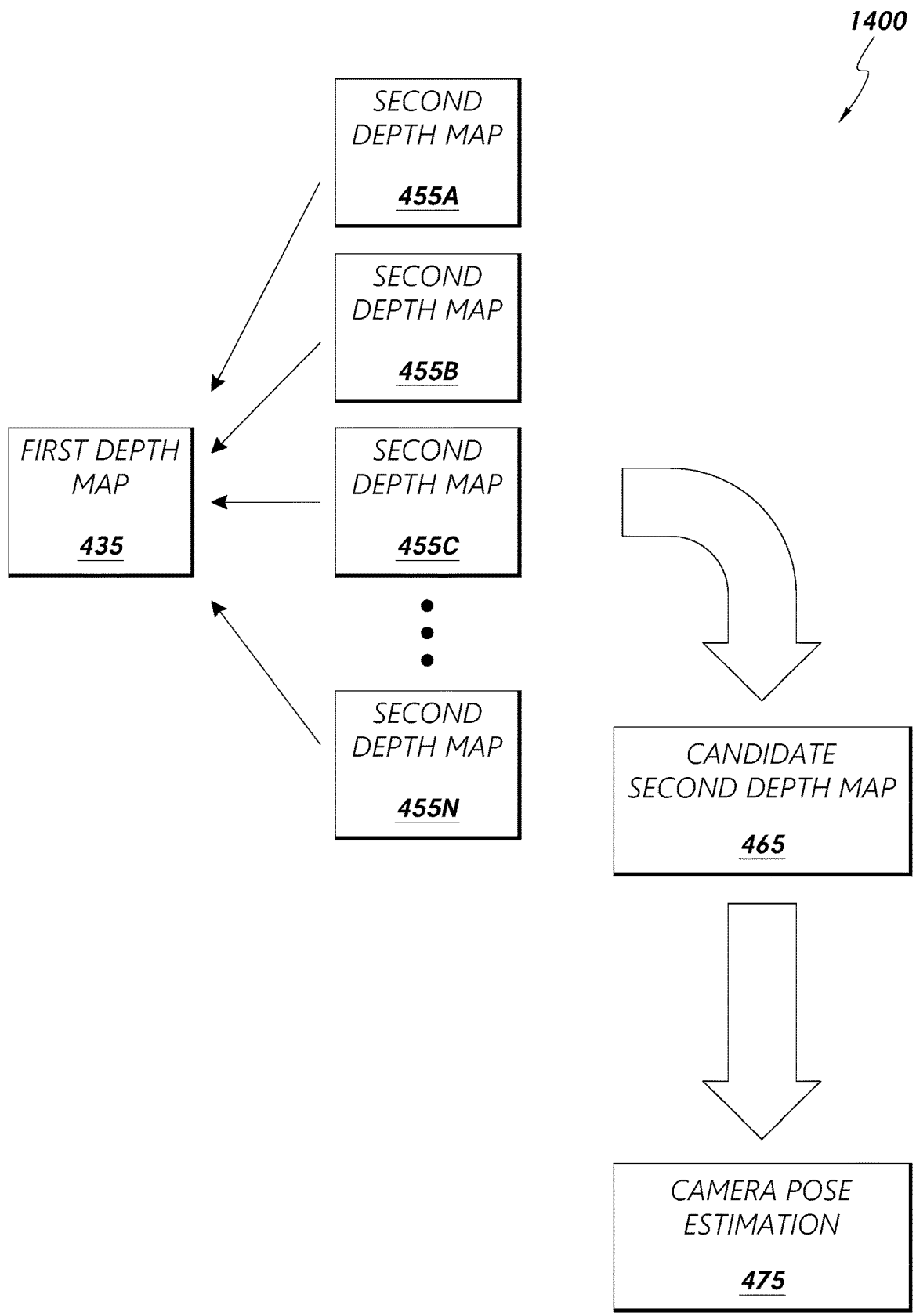
FIG. 14 illustrates a block diagram of an example image conversion process.

As discussed, one of the multiple second depth maps 455 may have a higher similarity of shape to a first depth map 435 than any of the other second depth maps 455. Referring to FIG. 14 image-based data analysis (e.g., image registration techniques) by the localization module 95 may include analyzing each of the second depth maps 455 generated from pre-operative CT scans (i.e., image data 91) as compared to a first depth map 435 (i.e., image data 92) captured by the imaging device 315 of an instrument positioned within a luminal network 130. For example, each of the plurality of second depth maps (455A, 455B, 455C . . . 455N) that are generated from the CT image data 91 are analyzed against the first depth map 435 that is generated from video image data 92 for similarity of shape. The analysis may include a comparison of identified features of the second depth map 455 to corresponding identified features of the first depth map 435 for similarity. As part of the analysis/comparison, the second depth map (455A, 455B, 455C . . . 455N) that has a highest similarity of shape to the first depth map 435 is identified. This second depth map 455 is identified by the localization module 95 as a "candidate" second depth map 465. The candidate second depth map 465 is used to generate the camera pose estimation 475, which is output as a virtual representation of the location (and orientation) of the medical instrument 34 within the luminal network 130.

A virtual camera pose 475 in CT coordinate space can be defined as

T(x, y, z, q)

where x, y, z are Cartesian coordinates of the estimated camera location 475 and q is the quaternion that represents camera orientation. For instance, a medical instrument (e.g., endoscope 52) can be articulable, such as with respect to at least a distal portion of the scope 52, so that the scope 52 can be steered within the human anatomy. In some embodiments, the scope 52 is configured to be articulated with, for example, five degrees of freedom, including XYZ coordinate movement in translation, as well as pitch and yaw in orientation. In some embodiments, the needle sensor provides six degrees of freedom, including X, Y, and Z ordinate positions, as well as pitch, roll, and yaw. Position sensor(s) of the scope 52, if present, may likewise have similar degrees of freedom with respect to the position information they produce/provide. The tip of the scope 52 can be oriented with zero deflection relative to a longitudinal axis thereof (also referred to as a "roll axis").

The camera pose T at each time point can be considered as a function of virtual (i.e., second) depth map 455 $Z^{CT}$. Given an initial guess of the camera pose on startup, an optimization process outputs the optimal $\Delta T'$ that gives the highest similarity between the virtual (i.e., second) depth map 455 and video (i.e., first) depth map 435 as $$\Delta T'_{t+1|t} = \operatorname*{argmin}_{\Delta T_{t+1|t}} \{S^{-1}(Z_{t+1}, Z^{CT}(T_t + \Delta T_{t+1|t}))\} \quad (1)$$

$$T_{t+1} = T_t + \Delta T'_{t+1|t} \quad (2)$$

where camera pose at time t, $T_t$ is used for initializing the pose at time t+1, $T_{t+1}$. S is a similarity measure.

At the beginning of the medical procedure when the medical instrument (e.g., bronchoscope 52) is pointing into the luminal network 130 (for instance at the main carina of the trachea), the camera pose can be initialized with the midpoint in the centerline of the trachea for convenience. During the procedure, the optimal pose value 475 of the previous video image 92, estimated using the vision-based approach can be used to initialize the pose optimization process for the current video frame. Alternatively, other available sensory inputs such as EM data, position sensor data, or shape sensing data, for example, can also be incorporated for initializing the pose optimization process to achieve better robustness and accuracy.

Iterative optimization approaches or CNN-based pose estimators are applicable for solving Equation (1) above. Discrete optimization approaches including Powell optimization, Kalman filter based optimization, and Particle Swarm optimization can iteratively find the minimum of a scalar similarity function given a search space for the camera pose. The second depth map 455 that results in the minimum is the identified candidate second depth map 455, whose corresponding camera pose is then identified as the optimal pose 475. Normalized-cross correlation or mutual information can be used as the similarity function to compare second depth maps 455 to the first depth map 435, for example.

Figure 15:
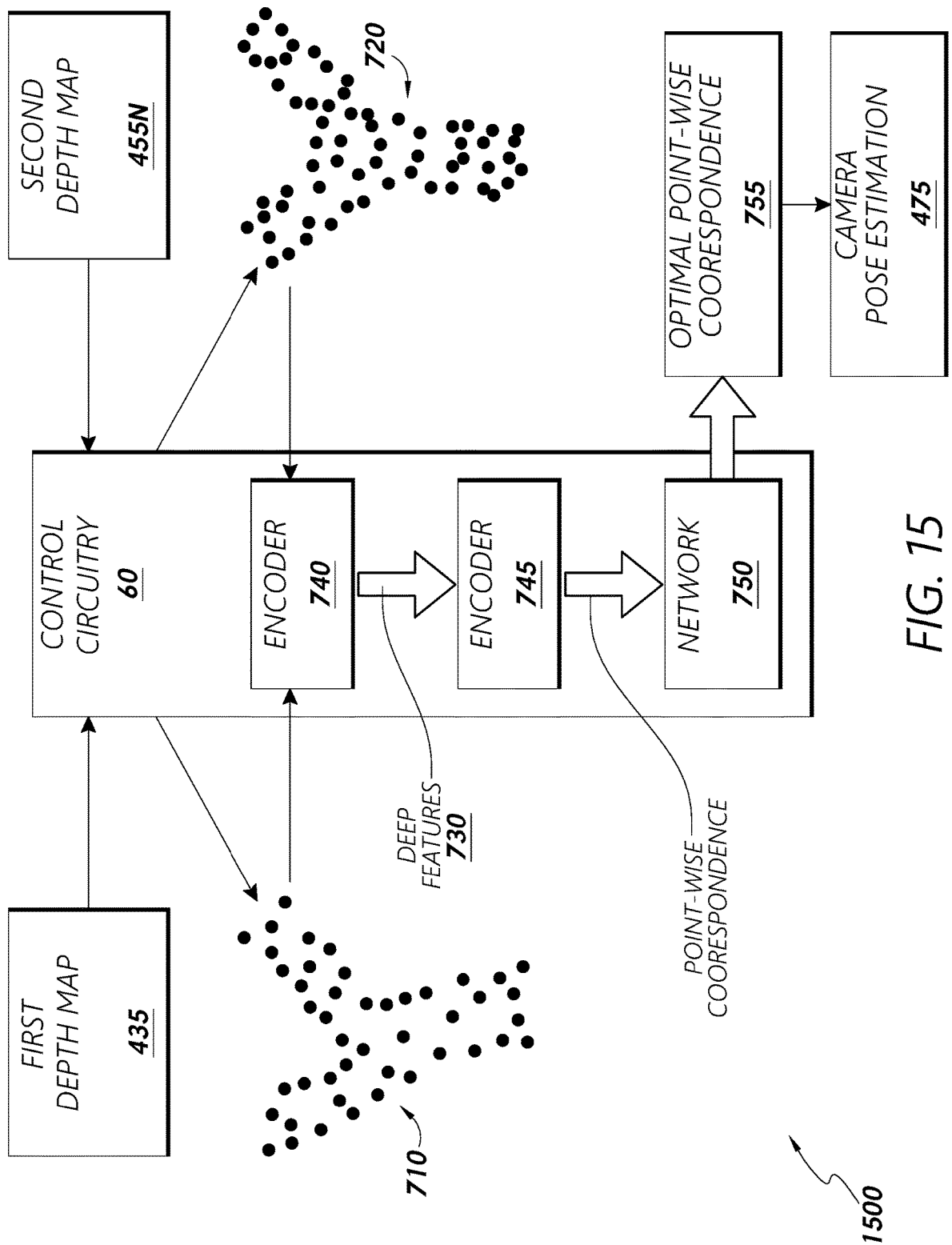
FIG. 15 illustrates a block diagram of an example camera pose estimation process.

Alternatively, CNN can be employed to estimate the camera pose 475 parameters by solving the transformation matrix between a 3D point cloud of the airway model and the point cloud inverse projected from the first depth map 435. For example, as shown in FIG. 15, the control circuitry 60 can be further configured to represent the first depth map 435 with a first point cloud 710 and the plurality of second depth maps 455 with a second point cloud 720. Point clouds of the second depth maps 455 can be combined/merged into one point cloud (i.e., the second point cloud 720). The control circuitry 60 can be further configured to determine deep features 730 based at least in part on the first 710 and second 720 point clouds using a first neural network. For example, a CNN encoder 740 can be used to extract deep features 730 from the point clouds 710 and 720, where deep features 730 represent the geometric features of the point clouds 710 and 720. Then another CNN encoder 745 can be used to propose correspondence between the key points 730 of the point clouds 710 and 720 by searching in the shared feature space. For example, the control circuitry 60 can be configured to establish the point-wise correspondence by searching in a shared feature space using a second neural network 745, where the shared feature space is relative to the deep features 730. The point-wise correspondence can then be passed into another network 750 (such as a differentiable RANSAC network, for example) to output the optimal point-wise correspondence 755, which can be used to calculate the optimal transformation to be applied on the second point cloud to achieve the best registration between the first point cloud and the transformed second point cloud, as well as the highest similarity between the first depth map 435 and a second depth map 455N. The optimal camera pose 475 can be calculated from the optimal point-wise correspondence 755. In some cases, pose estimation based on CNNs can provide faster convergence than the iterative discrete optimization approaches.

CNN can also be used to generate efficient image encoding to find the optimal camera pose 475 by searching for the candidate second depth map 465. Given an airway model (e.g., first depth map 435), a dataset of paired virtual (second) depth maps 455 and camera poses 475 can be pre-computed, relative to the first depth map 435. Image retrieval techniques can be applied to find the depth map 455 in the dataset with the highest similarity to the video depth map 435, which becomes the candidate depth map 465. The camera pose value 475 of the candidate depth map 465 can either be used as the optimal (i.e., output) camera pose 475 for the video frame or as a good initial value for fine-tuning the pose value for faster convergence. The relative pose between the candidate depth map 465 and the video depth map 435 can be estimated by passing them into a spatial transformation network that regresses the relative transformation between them.

Figure 16:
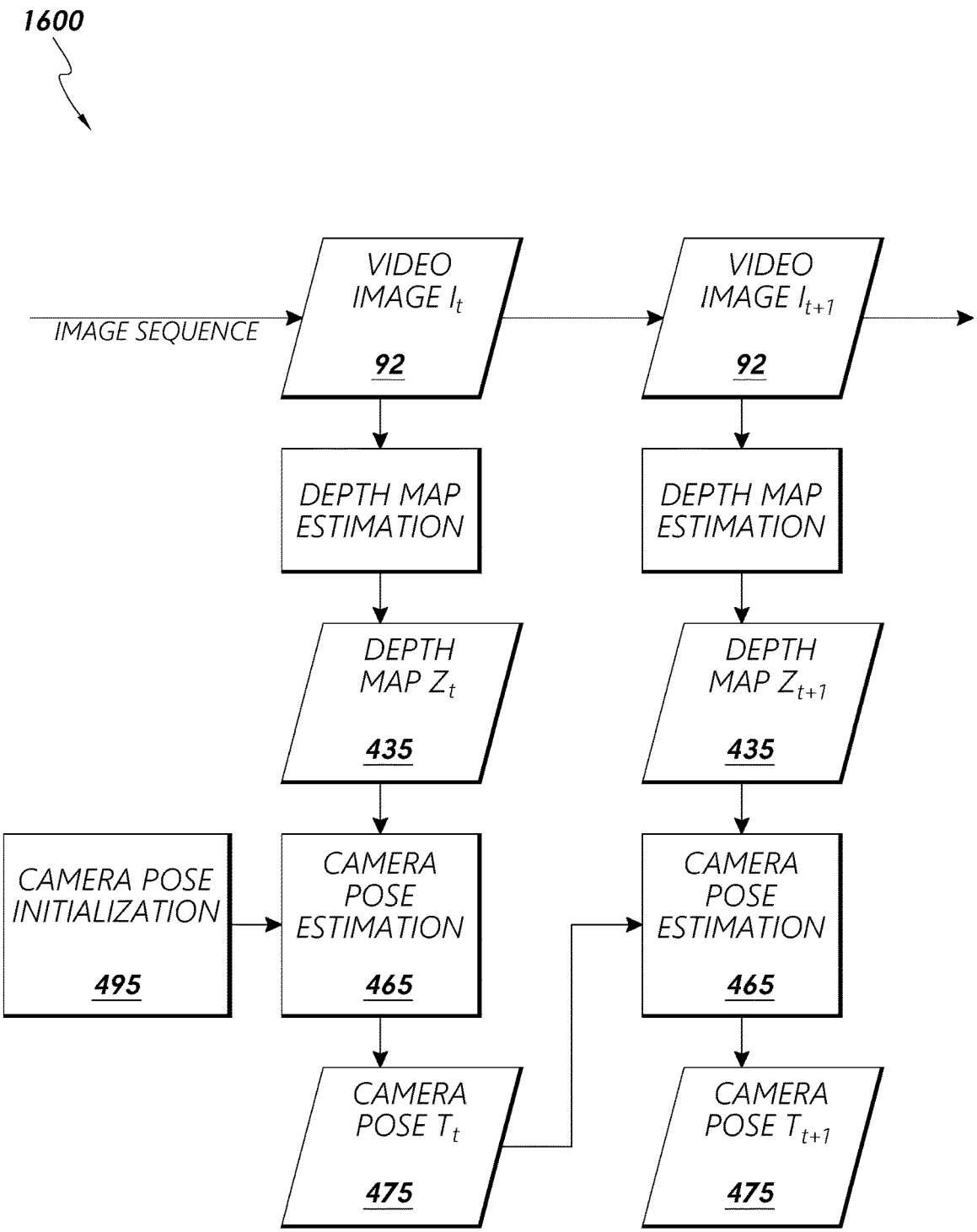
FIG. 16 depicts a flowchart illustrating an example method for image-based localization.

Referring to FIG. 16, in various embodiments, the process of generating second depth maps 455 and identifying one candidate depth map 465 of the plurality of second depth maps 455 is an iterative or continuous process 1600. For example, the process 1600 can include using the camera pose of the candidate depth map 465 from the plurality of second depth maps 455 of a previous timestamp to initialize generating the plurality of second depth maps 455 for the current timestamp. Further, the result of the camera pose estimation 475 of a previous timestamp initializes the camera pose estimation process for the current timestamp. Referring to the process 1600, for real-time localization/navigation, the imaging device 315 (e.g., camera) can continuously capture video images 92. For instance, a video image 92 ($I_t$) is captured at time t. A first depth map 435 ($Z_t$) is generated from the video image 92 ($I_t$). A plurality of second depth maps 455 are generated from pre-operative CT images 91 captured previously. Based on an initial guess camera pose estimation 495 (for the first iteration) to initialize the process, the plurality of second depth maps 455 are compared to the first depth map 435 ($Z_t$) for similarity of shape. One of the plurality of second depth maps 455 that has a highest similarity of shape to the first depth map 435 is identified as a candidate second depth map 465, and a candidate camera pose estimation. A camera pose 475 ($T_t$) is generated based at least in part on the identified candidate second depth map 465. At the next iteration, a next video image 92 ($I_{t+1}$) is captured at time t+1. A first depth map 435 ($Z_{t+1}$) is generated from the video image 92 ($I_{t+1}$). A plurality of second depth maps 455 are generated from pre-operative CT images 91 captured previously. The camera pose 475 ($T_t$) from the previous iteration at time t is used to initialize the current iteration at time t+1. Based on the camera pose 475 ($T_t$) to initialize the process, the plurality of second depth maps 455 are compared to the first depth map 435 of the current iteration (at time t+1) for similarity of shape. One of the plurality of second depth maps 455 that has a highest similarity of shape to the first depth map 435 ($Z_{t+1}$) is identified as a candidate second depth map 465, and a candidate camera pose estimation. A camera pose 475 ($T_{t+1}$) is generated based at least in part on the identified candidate second depth map 465. The iterative process can continue if desired using the current camera pose 475 ($T_{t+1}$) to initialize a next iteration.

4. Implementing Systems and Terminology

Implementations disclosed herein provide systems, methods and apparatus for image-based localization and navigation for robotically-controlled or user-controlled medical instruments. Various implementations described herein provide for improved navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

ADDITIONAL EMBODIMENTS

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method, comprising:
   generating a camera pose representative of a spatial location within an internal anatomical structure and capturing video image data of the internal anatomical structure, comprising:
   transforming the video image data into a first depth map of the internal anatomical structure, via a mapping function;
   receiving a plurality of second depth maps based at least in part on transformed computed tomography (CT) image data, each of the second depth maps representing a virtual model of the internal anatomical structure;
   identifying one of the plurality of second depth maps that has a highest similarity of shape to the first depth map; and
   generating the camera pose based at least in part on the identified one of the plurality of second depth maps, including estimating camera pose parameters by solving a transformation matrix between a 3D point cloud of the virtual model of the internal anatomical structure and a point cloud inverse projected from the first depth map.

2. The method of claim 1, further comprising forming the first depth map from the video image data using a convolutional neural network (CNN).

3. The method of claim 1, wherein a convolutional neural network (CNN) is employed to solve the transformation matrix and estimate the camera pose parameters.

4. The method of claim 1, further comprising identifying a desired location in the one of the plurality of second depth maps that corresponds to a location in one or more video images, using the first depth map.

5. The method of claim 1, wherein the identifying one of the plurality of second depth maps is an iterative or continuous process.

6. The method of claim 5, wherein the iterative process includes using the camera pose of one of the plurality of second depth maps of a previous iteration to initialize generating the plurality of second depth maps.

7. The method of claim 1, further comprising generating the plurality of second depth maps using a plurality of virtual camera poses.

8. The method of claim 1, wherein the camera pose comprises a virtual spatial estimation representative of a physical spatial location within the internal anatomical structure.

9. The method of claim 8, further comprising defining the camera pose in coordinates relative to the CT image data.

10. A method, comprising:
    generating a camera pose representative of a spatial location within a bronchial airway and capturing video image data of the bronchial airway, comprising:
    transforming the video image data into a first depth map of the bronchial airway, via a mapping function;
    receiving a plurality of second depth maps based at least in part on computed tomography (CT) image data, each of the second depth maps representing a virtual model of the internal anatomical shape structure of the bronchial airway;
    identifying one of the plurality of second depth maps that has a highest similarity of shape to the first depth map;
    estimating camera pose parameters by solving a transformation matrix between a 3D point cloud of the virtual model of the internal anatomical structure and a point cloud inverse projected from the first depth map; and
    generating the camera pose representing a location and an orientation having six-degrees of freedom (6DoF) within the bronchial airway, based at least in part on the identified one of the plurality of second depth maps.

11. The method of claim 10, further comprising forming the first depth map using the video image data with a convolutional neural network (CNN) that performs domain adaptation.

12. The method of claim 11, further comprising learning the mapping function by the CNN with supervised learning by pairing video image data to corresponding first depth maps, where the first depth maps are formed as a function of the video image data.

13. The method of claim 11, further comprising learning a mapping function by the CNN with unsupervised generative adversarial learning with a cyclic consistency that does not require paired data, where the first depth map is formed as a function of the video image data.

14. The method of claim 11, further comprising pre-computing a dataset comprised of paired second depth maps and virtual camera poses, relative to the first depth map.

15. The method of claim 14, further comprising applying image registration techniques to find a candidate second depth map relative to the dataset with a highest similarity of shape to the first depth map.

16. The method of claim 15, further comprising using a virtual camera pose value of the candidate second depth map as the camera pose or as an initial value for a candidate virtual camera pose for iteratively generating a next plurality of second depth maps.

17. The method of claim 15, further comprising estimating a relative pose between the candidate second depth map and the first depth map by passing the candidate second depth map and the first depth map into a spatial transformation network configured to regress a relative transformation between the candidate second depth map and the first depth map.

18. A medical system, comprising:
a medical instrument having a camera associated with a distal end thereof, the camera configured to capture video image data of an internal anatomical structure; and
control circuitry communicatively coupled to the medical instrument, the control circuitry being configured to:
transform the video image data into a first depth map that characterizes the internal anatomical structure based at least in part on a mapping function;
receive a plurality of second depth maps based at least in part on computed tomography (CT) image data, each of the second depth maps representing a virtual model of the internal anatomical structure;
identify one the plurality of second depth maps that has a highest similarity of shape to the first depth map;
estimate camera pose parameters by solving a transformation matrix between a 3D point cloud of the virtual model of the internal anatomical structure and a point cloud inverse projected from the first depth map; and
generate a camera pose representing a location and an orientation having six-degrees of freedom (6DoF) within the internal anatomical structure, based at least in part on the identified one of the plurality of second depth maps.

19. The medical system of claim 18, wherein the control circuitry is further configured to represent the first depth map with a first point cloud and a second depth map of the plurality of second depth maps with a second point cloud.

20. The medical system of claim 19, wherein the control circuitry is further configured to determine deep geometric features based at least in part on the first and second point clouds using a first neural network.

21. The medical system of claim 20, wherein the control circuitry is further configured to establish a point-wise correspondence between a plurality of key points of the first point cloud and an associated plurality of key points of the second point cloud.

22. The medical system of claim 21, wherein the control circuitry is further configured to establish the point-wise correspondence by searching in a shared feature space using a second neural network, the shared feature space relative to the deep geometric features.

23. The medical system of claim 21, wherein the control circuitry is further configured to pass the point-wise correspondence into another network to output a second point-wise correspondence.

24. The medical system of claim 23, wherein the other network comprises a differentiable random sample consensus (RANSAC) network.

25. The medical system of claim 23, wherein the control circuitry is further configured to generate the camera pose based at least in part on the second point-wise correspondence.

26. A medical system, comprising:
a means for capturing video image data of an internal anatomical structure;
a means for transforming the video image data into a first depth map that characterizes the internal anatomical structure based at least in part on a mapping function;
a means for receiving a plurality of second depth maps based at least in part on transformed computed tomography (CT) image data, each of the second depth maps representing a virtual model of the internal anatomical structure;
a means for identifying one of the plurality of second depth maps that has a highest similarity of shape to the first depth map; and
a means for generating a camera pose based at least in part on the identified one of the plurality of second depth maps, including estimating camera pose parameters by solving a transformation matrix between a 3D point cloud of the virtual model of the internal anatomical structure and a point cloud inverse projected from the first depth map.

27. The medical system of claim 26, further comprising an additional means for forming the camera pose using at least one of electromagnetic (EM) data, kinematic data, inertial measurement data, or shape sensing data.

28. The medical system of claim 26, further comprising a means for communicating the camera pose in real time, relative to the internal anatomical structure.

29. The medical system of claim 28, wherein the internal anatomical structure is intermittently in motion.

* * * * *